(12) United States Patent
Kar et al.

(10) Patent No.: US 8,652,373 B2
(45) Date of Patent: Feb. 18, 2014

(54) HYDROXYAPATITE POLY(ETHERETHERKETONE) NANOCOMPOSITES AND METHOD OF MANUFACTURING SAME

(75) Inventors: Kamal Krishna Kar, Kanpur (IN); Sumit Pramanik, Kanpur (IN)

(73) Assignee: Indian Institute of Technology Kanpur, Kanpur (IN)

( * ) Notice: Subject to any disclaimer, the term of this patent is extended or adjusted under 35 U.S.C. 154(b) by 145 days.

(21) Appl. No.: 13/147,502

(22) PCT Filed: Sep. 20, 2010

(86) PCT No.: PCT/IB2010/054234
§ 371 (c)(1),
(2), (4) Date: Aug. 2, 2011

(87) PCT Pub. No.: WO2012/004637
PCT Pub. Date: Jan. 12, 2012

(65) Prior Publication Data
US 2012/0107612 A1 May 3, 2012

(30) Foreign Application Priority Data
Jul. 9, 2010 (IN) .......................... 1614/DEL/2010

(51) Int. Cl.
*B32B 9/04* (2006.01)
(52) U.S. Cl.
USPC .......................... 264/122; 264/115; 264/138
(58) Field of Classification Search
USPC ............................. 264/115, 122, 138
See application file for complete search history.

(56) References Cited

U.S. PATENT DOCUMENTS

| 4,323,211 | A | * | 4/1982 | Bambara et al. | .......... 246/169 A |
| 5,679,294 | A | * | 10/1997 | Umezu et al. | ................ 264/628 |
| 6,387,414 | B1 | * | 5/2002 | Akashi et al. | ............... 424/602 |
| 7,230,039 | B2 | | 6/2007 | Trieu et al. | |
| 7,498,043 | B2 | * | 3/2009 | Sayer et al. | ................... 424/426 |
| 7,871,638 | B2 | * | 1/2011 | Tanaka et al. | ................ 424/423 |
| 8,287,914 | B2 | * | 10/2012 | Riman et al. | ................. 424/602 |
| 2002/0127262 | A1 | * | 9/2002 | Akashi et al. | ............... 424/423 |
| 2004/0236432 | A1 | * | 11/2004 | Hyon et al. | ................ 623/23.51 |
| 2005/0244449 | A1 | * | 11/2005 | Sayer et al. | .................... 424/422 |
| 2006/0165663 | A1 | * | 7/2006 | Tanaka et al. | ................ 424/93.7 |
| 2007/0196509 | A1 | * | 8/2007 | Riman et al. | ................. 424/602 |
| 2009/0155320 | A1 | * | 6/2009 | Rudin et al. | ................. 424/401 |
| 2010/0040668 | A1 | * | 2/2010 | Riman et al. | ................. 424/426 |
| 2010/0172955 | A1 | * | 7/2010 | Bratt et al. | .................... 424/423 |

FOREIGN PATENT DOCUMENTS

JP 2001-026408 1/2001

OTHER PUBLICATIONS

Tamai et al. "Preparation of Polymer Particles Coated with Hydroxyapaite" Journal of Colloid and Interface Science 212, 585-588 (1999).*

Tanahashi et al. "Apatite Coating on Organic Polymers by a Biometric Process". J. Am. Ceram. Soc, 77 [11] 2805-2808 (1994).*

(Continued)

*Primary Examiner* — Matthew Daniels
*Assistant Examiner* — Saeed Huda
(74) *Attorney, Agent, or Firm* — Foley & Lardner LLP

(57) ABSTRACT

Hydroxyapatite-polymer nanocomposites, which are nanoparticles/microparticles, methods for making them, and articles made from them are disclosed. These methods are capable of preparing nanocomposites exhibiting more homogeneous dispersion of nanoparticles than is seen using previous methods. Such nanocomposites and articles are useful for a wide variety of applications, such as biological, medical, biochemical, biosensor, fuel cell, and aerospace applications.

13 Claims, 32 Drawing Sheets

(56) References Cited

OTHER PUBLICATIONS

Bakar, M.S.A. et al., "Mechanical properties of injection molded hydroxyapatite-polyetheretherketone biocomposites," Composites Science and Technology, 2003, vol. 63, pp. 421-425.

Bakar, M.S.A. et al., "Tensile properties and microstructural analysis of spheroidized hydroxyapatite-poly (etheretherketone) biocomposites," Materials Science and Engineering, 2003, vol. 345, pp. 55-63.

Bakar, M.S.A. et al., "Tensile properties, tension-tension fatigue and biological response of polyetheretherketone-hydroxyapatite composites for load-bearing orthopedic implants," Biomaterials, 2003, vol. 24, pp. 2245-2250.

Bakar, M.S.A. et al., "Thermal processing of hydroxyapatite reinforced polyetheretherketone composites," Journal of Materials Processing Technology, 1999, vol. 89-90, pp. 462-466.

Bonfield, W. et al., "Hydroxyapatite reinforced polyethylene—a mechanically compatible implant material for bone replacement," Biomaterials, Jul. 1981, vol. 2, pp. 185-186.

Fan, J.P. et al., "Influence of interphase layer on the overall elasto-plastic behaviors of HA/PEEK biocomposite," Biomaterials, 2004, vol. 25, pp. 5363-5373.

Fan, J.P. et al., "Modeling of the mechanical behavior of HA/PEEK biocomposite under quasi-static tensile load," Materials Science and Engineering, 2004, vol. 382, pp. 341-350.

Ha, S-W. et al., "Surface activation of polyetheretherketone (PEEK) and formation of calcium phosphate coatings by precipitation," J. Mater. Sci. Mater. Med., 1997, vol. 8, pp. 683-690.

International Search Report and Written Opinion for PCT/IB2010/054234 mailed Jan. 13, 2011.

Meenan, B.J. et al., "Thermal analysis studies of poly(etheretherketone)/hydroxyapatite biocomposite mixtures," J. Mater. Sci. Mater. Med., 2000, vol. 11, pp. 481-489.

Pramanik, S. et al., "Synthesis and Characterizations of Hydroxyapatite-Poly(ether ether ketone) Nanocomposite: Acellular Simulated Body Fluid Conditioned Study," ICBME 2008, Proceedings 23, 2009, pp. 1309-1312.

Rajkumar, M. et al., "In-situ preparation of hydroxyapatite nanorod embedded poly (vinyl alcohol) composite and its characterization," International Journal of Engineering Science and Technology, 2010, vol. 2, No. 6, pp. 2437-2444.

Tan, K.H. et al., "Fabrication and characterization of three-dimensional poly(ether-ether-ketone)/-hydroxyapatite biocomposite scaffolds using laser sintering," Proc. Inst. Mech. Eng. H., 2005, vol. 219, pp. 183-194.

Tan, K.H. et al., "Scaffold development using selective laser sintering of polyetheretherketone-hydroxyapatite biocomposite blends," Biomaterials, 2003, vol. 24, pp. 3115-3123.

Tang, S.M. et al., "Tension-tension fatigue behavior of hydroxyapatite reinforced polyetheretherketone composites," International Journal of Fatigue, 2004, vol. 26, pp. 49-57.

Yu, S. et al., "In vitro apatite formation and its growth kinetics on hydroxyapatite/polyetheretherketone biocomposites," Biomaterials, 2005, vol. 26, pp. 2343-2352.

* cited by examiner

HYDROXYAPATITE POLY(ETHERETHERKETONE) NANOCOMPOSITES AND METHOD OF MANUFACTURING SAME

This application is a U.S. national stage application claiming the benefit of International Patent Application No. PCT/IB2010/054234, filed on Sep. 20, 2010, which in turn claims the benefit of India patent application no. 1614/DEL/2010, filed on Jul. 9, 2010, the entire disclosures of which are incorporated herein by reference for any and all purposes.

TECHNOLOGY

This technology generally relates to ceramic-polymer nanocomposites.

BACKGROUND

Hydroxyapatite-polymer nanocomposites are useful materials for applications such as bone implants, bioprostheses, soft tissue augmentation, biosensors, membranes, fuel cells, and aerospace applications. These nanocomposites can exhibit high strength, bioactivity, biocompatibility, and osteoconductivity due to the presence of the hydroxyapatite particulates and excellent toughness with choice of a proper polymer matrix. Polyetheretherketones are exemplary polymers for these applications because of their superior strength, toughness, and high temperature properties.

Preparation of suitable nanocomposites is complicated by the tendency of nanoparticles to agglomerate non-homogeneously. Non-homogeneous dispersion of nanoparticles can result during nanocomposite preparation, in particular where the nanoparticle loadings are high, i.e., more than about 7 wt %.

SUMMARY

In one aspect, a method is provided including precipitating a calcium apatite particle onto a surface of a polymer particle to form a composite particle, forming a pellet comprising at least two composite particles, and sintering the pellet to form a sintered pellet. In one embodiment, the precipitation is from a solution including a solvent, calcium oxide, and phosphoric acid. In some embodiments, the solvent includes water. In some embodiments, at least a portion of the sintering is performed either below and above a melting temperature of the polymer particle. In some embodiments, the sintering is performed both below and above a melting temperature of the polymer particle. In one embodiment, the sintering includes at least three intervals: a first interval of three hours at 320° C., a second interval of two hours at 345° C., and a third interval of 90 minutes at 370° C. In some embodiments, the polymer particles have a diameter from 400 nm to 2 microns. In other embodiments, the polymer particles have a diameter from 200 nm to 500 nm. In some embodiments, the polymer particle includes a thermoplastic polymer. In some embodiments, the thermoplastic polymer is a polyetheretherketone. In some embodiments, the calcium apatite particle includes hydroxyapatite. In some embodiments, the calcium apatite particle is nanocrystalline. In some embodiments, the diameter of the calcium apatite particles is less than 100 nm. In some embodiments, the diameter of the calcium apatite particles is from 5 nm to 70 nm.

In some embodiments, the precipitating includes biomimitic growth. In some embodiments, the forming includes milling the composite particle for at least 30 minutes. In some embodiments, the forming includes milling the composite particle for at least 1 hr. In some embodiments, the forming includes milling the composite particle for at least 1.5 hr. In some embodiments, the forming includes milling the composite particle for 2 hr. In some embodiments, the forming includes milling the composite particle from 30 minutes to 2 hrs. In some embodiments, where virgin polymer is used, no milling is required.

In some embodiments, the composite particle is a nanocomposite particle. In some embodiments, the composite particles have diameter from 500 nm to 12 microns.

In some embodiments, the composite particles have a ratio of calcium to phosphorous atoms from 1.5 to 1.8. In some embodiments, the composite particles include at least 40 wt % polymer and less than 60 wt % calcium apatite. In some embodiments, the composite particles include at least 50 wt % polymer and less than 50 wt % calcium apatite. In some embodiments, the composite particles include from 40 wt % to 99 wt % polymer and from 60 wt % to 1 wt % calcium apatite. In some embodiments, the amount of calcium apatite is varied from 0 to 1, 5, 10, 15, 20, 25, 30, 35, 40, 45, 50 to 100 wt %, with the amount of polymer in the composite is changed from 100 to 99, 95, 90, 85, 80, 75, 70, 65, 60, 55, 50 to 0 wt %, respectively. In some embodiments, the composite contains from 5 wt % to 50 wt % calcium apatite. In some embodiments, where the polymer is virgin polymer, no calcium apatite is used.

In some embodiments, the pellets includes a shell surrounding a core, where the shell includes the calcium apatite and the core includes the polymer. In some embodiments, the sintering includes liquid phase sintering. As used herein, liquid phase sintering refers to a sintering process in which at least one component in the composite is in the liquid phase. In the composites described herein, the polymer is the component that is in the liquid phase above a given temperature. The liquid phase sintering improves the bonding property between the calcium apatite and the polymer particles.

In some embodiments, the sintered pellets include at least 30 wt % polymer and less than 70 wt % calcium apatite. In some embodiments the sintered pellets include at least 50 wt % polymer and less than 50 wt % calcium apatite. In some embodiments, the sintered pellets include from 30 wt % to 99 wt % polymer and from 70 wt % to 1 wt % calcium apatite. In some embodiments, the amount of calcium apatite is varied from 0 to 1, 5, 10, 15, 20, 25, 30, 35, 40, 45, 50 to 100 wt %, with the amount of polymer in the composite is changed from 100 to 99, 95, 90, 85, 80, 75, 70, 65, 60, 55, 50 to 0 wt %, respectively. In some embodiments, the composited contain from 5 wt % to 50 wt % calcium apatite. In some embodiments, where the polymer is virgin polymer, no calcium apatite is used.

In another aspect, a method is provided including precipitating a calcium apatite polymer onto a surface of a polymer particle to form a composite particle. In some embodiments, the method also includes forming a pellet from at least two of the composite particles. In some embodiments, the method also includes sintering the pellet to form a sintered pellet.

In another aspect, composite particles, pellets, and sintered pellets formed by any of the above methods are provided.

In another aspect, compositions are provided including a shell surrounding a core, where the shell includes a calcium apatite particle and the core includes a polymer, where the shell composition is richer in calcium apatite than in the polymer and where the core composition is richer in the polymer than in the calcium apatite. In some embodiments, the polymers are thermoplastic polymers. In some embodiments, the polymer includes polyetheretherketone. In some embodiments, the calcium apatite includes hydroxyapatite. In some embodiments, the calcium apatite is nanocrystalline.

In some embodiments, the calcium apatite includes hydroxyapatite crystals with a diameter less than 100 nm. In some embodiments, the composition is sintered. In some embodiments, the composition includes a ratio of calcium to phosphorous atoms from 1.5 to 1.8. In some embodiments, the composition include at least 30 wt % polymer and less than 70 wt % calcium apatite. In some embodiments the composition includes at least 50 wt % polymer and less than 50 wt % calcium apatite. In some embodiments, the composition includes from 34 wt % to 95 wt % polymer and from 66 wt % to 5 wt % calcium apatite. In some embodiments, the calcium apatite contacts the polymer.

In another aspect, articles including any of the above compositions are provided. In some embodiments, the articles have a diameter of greater than 1 μm and less than 10 μm. In some embodiments, the articles have a diameter of greater than 1 μm and less than 4 μm. In some embodiments, the articles have a diameter of greater than 1 μm and less than 2 μm. Such articles may be, for example, composite particles or pellets or sintered pellets. Other articles include, for example, bone implants, bioprostheses, biosensors, membranes, or fuel cells. Such articles are made from composite particles or pellets or sintered pellets.

PkHA15, (e) PkHA20, (f) PkHA25, (g) PkHA30, (h) PkHA35, (i) PkHA40, (j) PkHA45, (k) PkHA50, and (l) PkHA100.

Figure 27A:
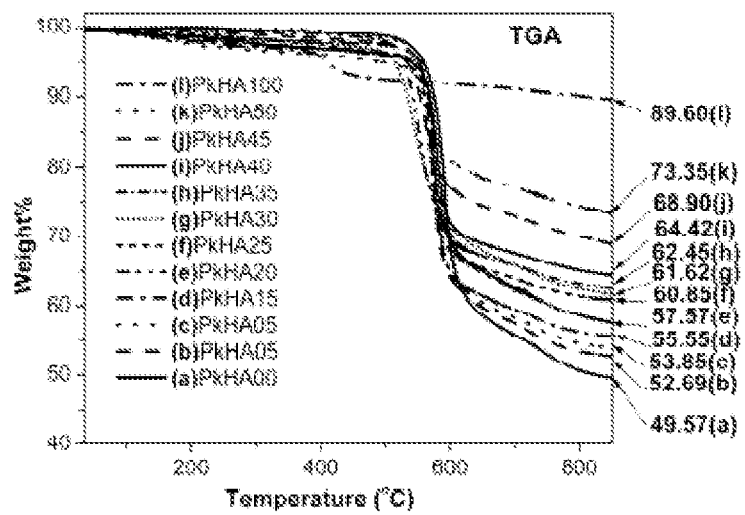
FIG. 27A displays sample weight as a function of temperature during thermal gravimetric analysis (TGA) for unsintered PEEK-hydroxyapatite nanocomposites. Samples IDs are from Table 1: (a) PkHA00, (b) PkHA05, (c) PkHA10, (d)
Figure 27B:
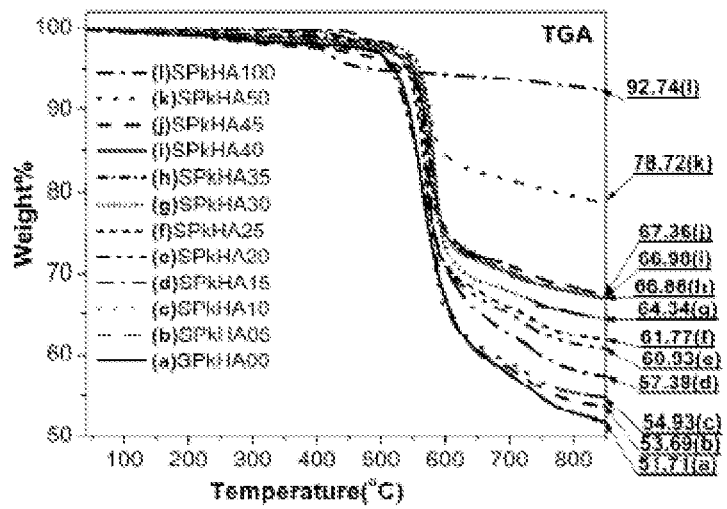

FIG. 27B displays sample weight as a function of temperature during TGA for sintered PEEK-hydroxyapatite nanocomposites. Samples IDs are from Table 4: (a) SPkHA00, (b) SPkHA05, (c) SPkHA10, (d) SPkHA15, (e) SPkHA20, (f) SPkHA25, (g) SPkHA30, (h) SPkHA35, (i) SPkHA40, (j) SPkHA45, (k) SPkHA50, and (l) SPkHA100.

DETAILED DESCRIPTION

In the following detailed description, the illustrative embodiments described in the detailed description, figures, and claims are not meant to be limiting. Other embodiments may be utilized, and other changes may be made, without departing from the spirit or scope of the subject matter presented here. In the description that follows, a number of terms are used extensively. The terms described below are more fully understood by reference to the specification as a whole. Units, prefixes, and symbols may be denoted in their accepted SI form.

The terms "a" and "an" as used herein mean "one or more" unless the singular is expressly specified. Thus, for example, reference to "a cell" includes a mixture of two or more cells, as well as a single cell.

In various aspects, composite materials and methods of their preparation are provided. As used herein, a composite material is one that is made from two or more individual materials, known as constituent materials, each of which has their own unique properties, but can combine to form one new material. The constituent materials remain distinguishable even after forming the composite. Examples of composite materials include synthetic composites such as e.g., fiberglass, concrete, paper, corrugated cardboard, and plywood, and naturally occurring composites such as e.g., wood and bone. There are two categories of constituent materials: matrix and reinforcement. The matrix material surrounds and supports the reinforcement materials by maintaining their relative positions. The matrix constituent material may, for example, provide scaffolding to support the reinforcing constituent material, provide impact resistance and toughness, provide high temperature resistance, and the like. Examples of matrix constituent material include polymers such as e.g., polyester, vinyl ester, epoxy, phenolic, polyimide, polyamide, polypropylene, and polyetheretherketone (PEEK), metals such as e.g., aluminum, magnesium, copper, magnesium, iron and titanium, and ceramics such as e.g., silicon carbide, calcium phosphate, hydroxyapatite, aluminum oxide, and silicon nitride. The reinforcements impart their special mechanical and physical properties to enhance the matrix properties. The reinforcing constituent material may, for example, provide increased electrical or thermal conductivity, provide improved mechanical strength, and so on. Examples of reinforcement constituent material include fibers, fillers and particles made from glass, metals such as boron, carbon, steel, copper, brass, lead and aluminum, minerals such as amorphous silica, asbestos, magnesium carbonate, kaolin, aluminum silicate, powdered quartz, mica, feldspar, and clay, and ceramics. A synergism of matrix and reinforcement constituent materials produces material properties unavailable from the individual constituent materials.

As further described below, some composites are also nanocomposites. As used herein, nanocomposites are composites, where at least one of the constituent materials has one, two, or three dimensions that are less than 100 nm. In some embodiments, the nanocomposites have a diameter from 5 nm to 100 nm. In some embodiments, at least one of the constituent materials is crystalline. Such crystalline materials may include nanocrystalline phases, which are crystalline phases having one, two, or three dimensions less than 100 nm. Examples of such nanocomposites include high density polyethylene matrix reinforced by cellulose nanocrystals, nanofibers made from tungsten carbide or silicon nitride, titanium oxide-siloxane nanocomposites, etc In some embodiments, the composites include polymer particles. Such polymer particles may include one or more polymers, copolymers, or blends of one or more polymers or copolymers. As used herein, the term polymer is inclusive of homopolymers which contain only a single type of monomer e.g., polystyrene; copolymers which containing two or more monomers e.g., ethyl-vinyl acetate; and blends which are made of two or more different species of polymers/copolymers, e.g., polyvinyl chloride-polyethylene blend. Such polymer particles may include one or more phases. For example, the polymer may include one or more crystalline phases. The polymer particles may optionally include one or more other constituents, such as but not limited to monomers; co-monomers; solvents; co-solvents; colorants; surfactants such as, but not limited to, alkyl propoxylated sulfates such as sodium alkyl propoxylated sulfate; stabilizers such as, but not limited to, amorphous propylene/ethylene (APE), amorphous propylene/butane, and polyacetal; binders such as, but not limited to, polyfunctional aziridine crosslinking agent, AIRFLEX® 105 vinyl acetate-ethylene (VAE) polymer emulsion, and polyvinyl alcohol (PVA); and the like. In some cases, polymer particles may include one or more thermoplastic polymers, i.e. a polymer that turns to a liquid when heated and freezes to a very glassy state when cooled sufficiently. Some thermoplastic polymers may be crystalline or semi-crystalline, and may exhibit a glass transition temperature and one or more melting temperatures. Both glass transition temperatures and melting temperatures may be determined, for example, using such methods as differential scanning calorimetry (DSC).

Various polymers known in the art can be employed in the composite materials of the present technology. Exemplary polymers include polyester, vinyl ester, epoxy, phenolic, polyimide, polyamide, polypropylene, and polyetheretherketone (PEEK). In some embodiments, the polymer of the composite is PEEK. In various embodiments of the composite material of the present technology, PEEK may be present as either a homopolymer, a co-polymer including etheretherketone repeat units e.g., PEEK-polydimethylsiloxane block copolymer, or as a blend including such homopolymers or copolymers, e.g., PEEK-poly(ethersulfone) blends. PEEK homopolymer is a semi-crystalline, thermoplastic polymer that exhibits a glass transition temperature and a melting temperature. PEEK may be represented by a structure depicting n etheretherketone units:

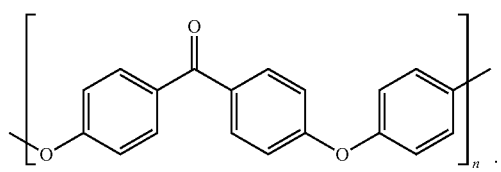

The PEEK has a range of melting temperatures, based upon the particular grade of PEEK, as is commonly understood. For example, the melting temperature may range from 330° C. to 390° C. or from 330° C. to 350° C. In some embodiments, the melting temperature of the PEEK is 335° C. On such PEEK polymer, having a melting temperature of 335° C. is commercially available as G-PEEK™, powder form, from Gharda Chemicals Limited, India.

In some embodiments, the composites include calcium apatite particles. Calcium apatites are a broad class of compounds that includes phosphate minerals such as, but not limited to, hydroxyapatite, fluoroapatite, chloroapatite, bromoapatite, and iodoapatite. Such calcium apatite particles may be naturally occurring minerals, or may be synthesized from mineral or non-mineral raw materials or intermediates. For example, hydroxyapatite particles may be synthesized by the reaction of calcium oxide and phosphoric acid, as reflected in equation (1):

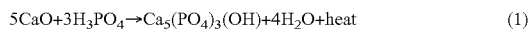
$$5CaO + 3H_3PO_4 \rightarrow Ca_5(PO_4)_3(OH) + 4H_2O + \text{heat} \tag{1}$$

where $Ca_5(PO_4)_3(OH)$ is the theoretical chemical formula for hydroxyapatite.

In some embodiments, the methods include precipitating a calcium apatite particle onto a surface of a polymer particle to form a composite particle. Any suitable polymer, such as those described above, may be used in the present methods. In an illustrative embodiment, the polymer is PEEK and it forms a composite with calcium apatite. In an illustrative embodiment, phosphoric acid and water may be added to an agitated slurry including a calcium oxide aqueous solution and PEEK polymer particles, so that calcium apatite particles precipitate on the surface of the PEEK polymer particles. Such precipitation of the calcium apatite particle includes particle nucleation and growth. The mechanism of such growth may resemble that of the biomimetic growth of host tissues on biomaterials. Such precipitated particles may include one or more nanocrystalline phases.

In some embodiments, methods of producing calcium apatite particles is provided. In other embodiments, methods of producing composites of polymers and calcium apatite are provided. In some embodiments of the method, the mineral or non-mineral raw materials or intermediates, such as but not limited to calcium oxide, calcium hydroxide, calcium carbonate, calcium nitrate, calcium acetate, calcium chloride, phosphoric acid, ammonium phosphate, dicalcium phosphate dihydrate, octacalcium phosphate, ammonium hydroxide, sodium hydroxide, and polymers such as PEEK, are dissolved in one or more solvents or co-solvents, and the calcium apatite is precipitated from solution. This may be accomplished through use of one or more suitable solvents or co-solvents, such as but not limited to water, alcohols such as methanol, ethanol and propanol, and ketones such as acetone. In some embodiments, such solvents or co-solvents include water. Raw materials or intermediates that are liquids may be supplied in their liquid forms or as solutions. Raw materials or intermediates that are solids may be supplied as solids, as slurries or pastes, or as solutions. In addition to any solvents or co-solvents that may be supplied with the raw materials or intermediates, any of these or other solvents or co-solvents may also be supplied separately, either at the start of the process, during the process, or both. In some embodiments, one or more of the raw materials or intermediates and solvents or co-solvents may be provided as a first solution and one or more of the other raw materials or intermediates or solvents or co-solvents may be subsequently added to the first solution. For example, a first solution may comprise a slurry of calcium oxide, and a solution of phosphoric acid and water may be added to the first solution to produce calcium apatite particles.

Figure 1:
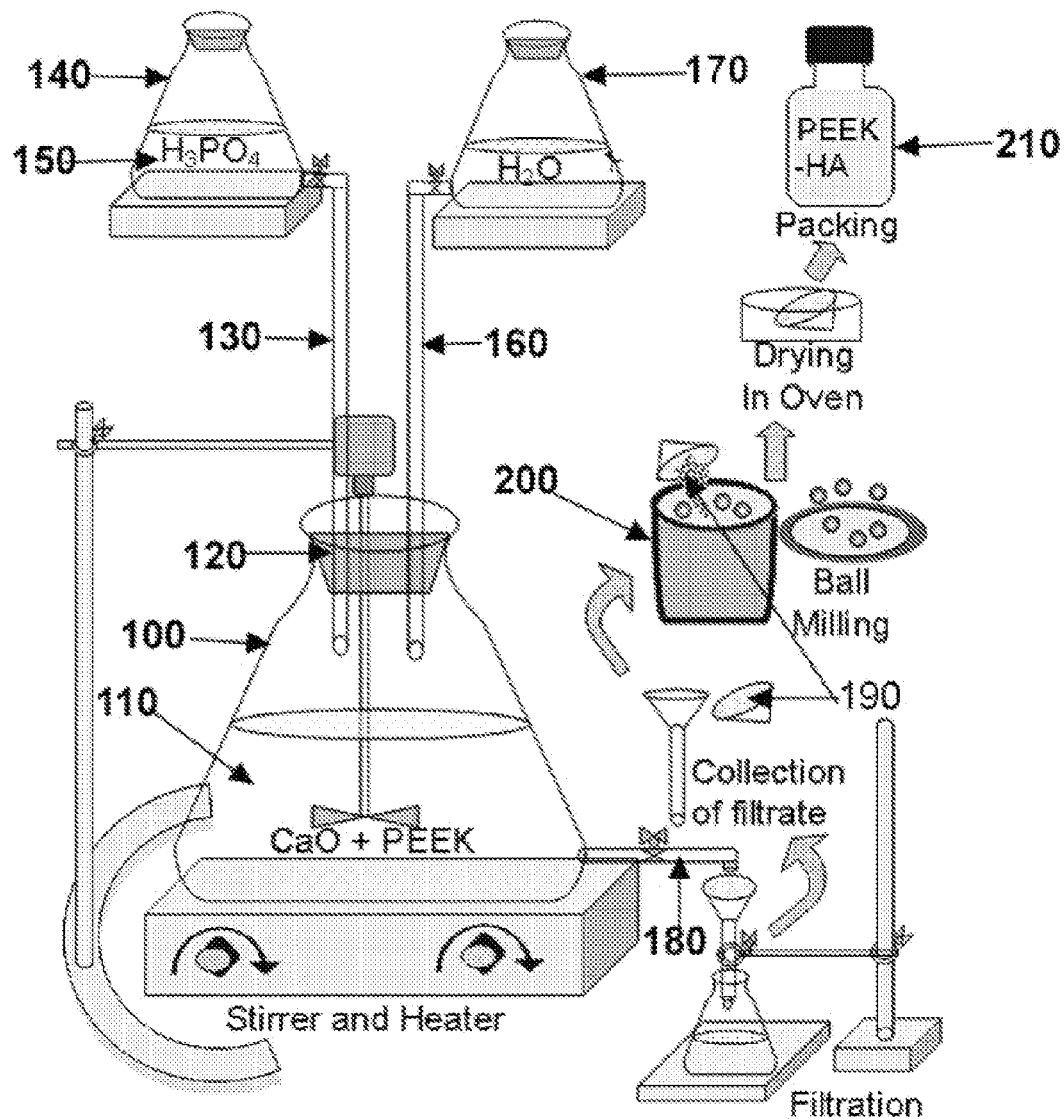
FIG. 1 depicts a schematic of one embodiment of a method of making polyetheretherketone (PEEK)-hydroxyapatite nanocomposites.

FIG. 1 depicts a schematic of an illustrative embodiment of a method of making polyetheretherketone (PEEK)-hydroxyapatite nanocomposites. Flask 100 carries a solution 110 of calcium oxide (CaO) and PEEK in a solvent such as water. Flask 100 may alternatively carry a solution containing only PEEK or only CaO for conducting comparative experiments. The flask is connected to a heating and stirring assembly. The flask has stopper 120 with two tubes passing through it and ending just above the solution 110. Tube 130 is connected to the bottom of flask 140, which carries a phosphoric acid solution 150. Tube 160 is connected to the bottom of flask 170, which carries water. Phosphoric acid from flask 140 is added dropwise through the tube 130 to the solution 110, whereby the composite is precipitated. The solution including the precipitate is carried through tube 180 to a filter assembly, where it is filtered and the filtrate collected as composite material 190. The collected composite material is subjected to ball milling in apparatus 200. The resulting milled composite material is dried in the oven and packed and shipped as PEEK-hydroxyapatite composite material 210.

In some embodiments, composite materials including calcium apatite particles on the surface of a polymer particle, such as PEEK, is provided. In some embodiments, pellets are provided that include at least two composite particles. The pellet/particle may be formed by such methods as, for example, pressure compaction, hot pressing, tumbling, vibration, shaking, paddle mixing, and the like. Pressure compaction methods include such methods as, for example, hot pressing, compounding, tableting, and the like. Formation of pellets/particles by tumbling, vibration, and shaking includes the use of single cone or double cone tumblers, rotary drums, inclined pans or disks, and the like. These and other agglomeration methods, as may be known, may be employed. The size of the pellet/particles may increase during such processing. After two hours of processing by, for example, ball milling, such a particle may grow to be larger than 1 μm or larger. For example, in some embodiments the particle may grow to be larger than 2 μm, larger than 4 μm, or larger than 8 μm in diameter. Such a particle may be smaller than 10 μm. For example in some embodiments, the particle is less than 5 μm, or less than 2 μm in diameter. In some embodiments, the particle is from 1 μm to 10 μm in diameter. In some embodiments, the particle is from 1 μm to 8 μm in diameter. In some embodiments, the particle is from 1 micron to 4 microns in diameter.

In some embodiments, the particles includes a shell surrounding a core, where the shell includes the calcium apatite and the core includes the polymer. The shell may include calcium apatite alone or a combination of calcium apatite and the polymer. In some embodiments, the composition of the shell may be richer in calcium apatite than the polymer. In other embodiments, the shell may be comprised entirely of calcium apatite. The core may include the polymer alone or a combination of calcium apatite and the polymer. In some embodiments, the composition of the core may be richer in polymer than in calcium apatite. In other embodiments, the core may be comprised entirely of the polymer. In an illustrative embodiment, the core may include PEEK and the shell may include calcium apatite.

In another aspect, the pellets as described above may be sintered. Thus, in one aspect, the technology provided sintered pellets as well as methods for their preparation. Such methods include the process of sintering the pellet. As used herein the term "sintering" refers to heat treating the pellets at temperatures sufficiently low to avoid significant agglomeration of the pellets. For example, in some embodiments, less than about 2%, less than about 5%, less than about 10% or less than about 20% of pellets agglomerate during sintering. In some embodiments, such sintering may be below the melting temperatures of all of the polymers in the pellets. In some embodiments, such sintering may be above the melting temperature of one or more polymers in the pellets, but below the melting temperature of one or more other polymers in the pellets. In some embodiments, such sintering may be above the melting temperatures of all of the polymers in the pellets. Sintering may also include successive sintering at more than one temperature. For example, sintering may include successive sintering below, at, and/or above one or more melting temperatures of polymers in the pellets. Sintering may include liquid sintering, where at least a portion of the pellet is liquid during the heating process. Sintering may optionally be accompanied by mechanical agitation, bubbling or fluidization by a gas, and the like. In some embodiments, the sintering includes liquid phase sintering. As used herein, liquid phase sintering refers to a sintering process in which at least one component in the composite is in the liquid phase. In the composites described herein, the polymer is the component that is in the liquid phase above a given temperature. The liquid phase sintering improves the bonding property between the calcium apatite and the polymer particles.

In one aspect, a method is provided including precipitating a calcium apatite particle onto a surface of a polymer particle to form a composite particle, forming a pellet comprising at least two composite particles, and sintering the pellet to form a sintered pellet. In one embodiment, the precipitation is from a solution including a solvent, calcium oxide, and phosphoric acid. In some embodiments, the solvent includes water. In some embodiments, at least a portion of the sintering is performed either below or above a melting temperature of the polymer particle. In some embodiments, the sintering is performed both below and above a melting temperature of the polymer particle. In one embodiment, the sintering includes at least three intervals: a first interval of three hours at 320° C., a second interval of two hours at 345° C., and a third interval of 90 minutes at 370° C. In some embodiments, the polymer particles have a diameter from 400 nm to 2 microns. In other embodiments, the polymer particles have a diameter from 200 nm to 2 microns. In other embodiments, the polymer particles have a diameter from 200 nm to 500 nm. In some embodiments, the polymer particle includes a thermoplastic polymer. In some embodiments, the thermoplastic polymer is a polyetheretherketone. In some embodiments, the calcium apatite particle includes hydroxyapatite. In some embodiments, the calcium apatite particle is nanocrystalline. In some embodiments, the diameter of the calcium apatite particles is less than 100 nm. In some embodiments, the diameter of the calcium apatite particles is from 5 nm to 70 nm.

In some embodiments, the precipitating includes biomimitic growth. In some embodiments, the forming includes milling the composite particle for at least 30 minutes. In some embodiments, the forming includes milling the composite particle for at least 1 hr. In some embodiments, the forming includes milling the composite particle for at least 1.5 hr. In some embodiments, the forming includes milling the composite particle for 2 hr. In some embodiments, the forming includes milling the composite particle from 30 minutes to 2 hrs. In some embodiments, where virgin polymer is used, no milling is required.

In some embodiments, the composite particle is a nanocomposite particle. In some embodiments, the composite particles have diameter from 100 nm to 1 microns. In some embodiments, the composite particles have diameter from 500 nm to 12 microns. In some embodiments, the composite particles have diameter from 100 nm to 2 microns.

In some embodiments, the composite particles have a ratio of calcium to phosphorous atoms between 1 and 2. In some embodiments, the composite particles have a ratio of calcium to phosphorous atoms between 1.5 and 1.8. In some embodiments, the composite particles include at least 40 wt % polymer and less than 60 wt % calcium apatite. In some embodiments, the composite particles include at least 50 wt % polymer and less than 50 wt % calcium apatite. In some embodiments, the composite particles include from 40 wt % to 99 wt % polymer and from 60 wt % to 1 wt % calcium apatite. In some embodiments, the amount of calcium apatite is varied from 0 to 5, 10, 15, 20, 25, 30, 35, 40, 45, 50 to 100 wt %, with the amount of polymer in the composite is changed from 100 to 95, 90, 85, 80, 75, 70, 65, 60, 55, 50 to 0 wt %, respectively. In some embodiments, the composite contains from 5 wt % to 50 wt % calcium apatite. In some embodiments, where the polymer is virgin polymer, no calcium apatite is used. In some embodiments, an article including the sintered pellet is provided, which is a nanocomposite particle and includes a minimum of 34% by wt and a maximum of 95% by wt of polymer and a minimum of 5% by weight and a maximum of 66% by wt of calcium apatite. In some embodiments, the article is greater than 1 micrometer and less than 10 micrometers in diameter.

In some embodiments, the pellets include a shell surrounding a core, where the shell includes the calcium apatite and the core includes the polymer. In some embodiments, the sintering includes liquid phase sintering. As used herein, liquid phase sintering refers to a sintering process in which at least one component in the composite is in the liquid phase. In the composites described herein, the polymer is the component that is in the liquid phase above a given temperature. The liquid phase sintering improves the bonding property between the ceramics and the polymer particles.

In some embodiments, the sintered pellets include at least 30 wt % polymer and less than 70 wt % calcium apatite. In some embodiments the sintered pellets include at least 50 wt % polymer and less than 50 wt % calcium apatite. In some embodiments, the sintered pellets include from 30 wt % to 99 wt % polymer and from 70 wt % to 1 wt % calcium apatite. In some embodiments, the amount of calcium apatite is varied from 0 to 1, 5, 10, 15, 20, 25, 30, 35, 40, 45, 50 to 100 wt %, with the amount of polymer in the composite is changed from 100 to 99, 95, 90, 85, 80, 75, 70, 65, 60, 55, 50 to 0 wt %, respectively. In some embodiments, the composited contain from 5 wt % to 50 wt % calcium apatite. In some embodiments, where the polymer is virgin polymer, no calcium apatite is used.

In another aspect, composite particles, pellets, and sintered pellets formed by any of the above methods are provided Applications of the described composite materials are varied. Thus, in one aspect, articles including any of the above compositions are provided. In some embodiments, the articles have a diameter of greater than 1 μm and less than 10 μm. In some embodiments, the articles have a diameter of greater than 1 μm and less than 4 μm. In some embodiments, the articles have a diameter of greater than 1 μm and less than 2 μm. Such articles may be, for example, composite particles or pellets or sintered pellets. Other articles include, for example, bone implants, bioprostheses, biosensors, membranes, or fuel cells.

The present composites include calcium apatite and a polymer. In some embodiments, calcium apatite may be present as a shell on a polymer core. Calcium apatite, in the present composites, may provide surfaces for adsorption of functional biomolecules, such as but not limited to protein, DNA, and the like. Because electrical properties of the apatite, such as resistivity or capacitance, may change upon adsorption of the biomolecules, these materials may be effectively employed in receptors or transducers of a biosensor.

The composite materials described herein are strong and tough materials, and they may be used as substitutes for hard tissue in applications such as joint implants. In bioprostheses, such materials may provide substitutes for the calcified mineral in human bone, breast tissue, ureteric calculi, heart valves, and the like. The materials may also be used to fill in and smooth soft tissue, providing cosmetic correction of pock marks or scars.

Non-biological applications are also contemplated. The present composites include a polymer such as PEEK in combination with calcium apatite. PEEK based polymers are excellent candidates for membranes in proton exchange membrane (PEM) fuel cells due to high thermal stability, high mechanical property and good proton conductivity. The presence of porous calcium apatite in the present PEEK-based polymers may enhance the proton exchange property of the membrane. For example, the present high crystallinity membranes may be used to suppress methanol crossover in direct methanol fuel cell applications.

Aerospace applications may be exploited in view of the high temperature stability of the composites. The present methods provide high-strength composites which include calcium apatite and a polymer such as PEEK. Because the melting temperature of PEEK is higher than other general purpose polymers, it can be used in high temperature structural applications in space craft. PEEK is increasingly used in the aerospace industry as a replacement for metal components, because of its high thermal stability and dimensional stability, high specific strength, very high resistance to chemicals, low moisture absorption and adsorption, minimum thermally induced microcraking, reprocessability/reworkability. PEEK has already been used in in-engine, pedal support, aircraft exterior and aircraft interior components due to its high specific strength and toughness properties. Therefore, the strength properties of the present PEEK/calcium apatite nanocomposites will enhance these applications.

The present technology, thus generally described, will be understood more readily by reference to the following examples, which are provided by way of illustration and are not intended to be limiting in any way.

EXAMPLES

The present technology is further illustrated by the following examples, which should not be construed as limiting in any way.

Example 1

Preparation of Composite Particle Samples

Twelve aqueous samples were prepared by adding polyetheretherketone (10 g, PEEK; the grade used was G-PEEK™ powder available from M/S Gharda Chemicals Limited, India), calcium oxide (CaO; 0 to 6 g), and phosphoric acid (0 to 8 g) to water (0 to 75 ml), according to the ratios described in Table 1, below. The aqueous samples were agitated at 50° C. to 60° C. at 600 rpm. The phosphoric acid added was 0.956 M $H_3PO_4$ for the 0 wt % to 50 wt % calcium apatite nanocomposites and was 11.88 M for the 100 wt % calcium apatite only. The samples were then filtered and the filtrate collected as composite particle samples.

Two additional samples were prepared. One contained only PEEK in water, with no CaO and no addition of phosphoric solution. The other contained no PEEK, but only CaO that had been treated with phosphoric solution. These samples were also filtered and the filtrate collected.

Table 1 summarizes the theoretical compositions of the prepared samples, based on the targeted amounts of raw materials in each composition.

TABLE 1

Compositions of Prepared Samples

| | Targeted Raw Material Usages | | | | | Sample Compositions | |
|---|---|---|---|---|---|---|---|
| Sample ID | CaO (g) | $H_3PO_4$ (g) | $H_3PO_4$* (M) | $H_2O$** (ml) | PEEK (g) | PEEK (wt %) | Hydroxyapatite (wt %) |
| PkHA00 | 0 | 0 | 0 | 0 | 10 | 100 | 0 |
| PkHA01 | 0.06 | 0.08 | 0.040 | 10 | 10 | 99 | 1 |
| PkHA05 | 0.309 | 0.419 | 0.05 | 10 | 10 | 95 | 5 |
| PkHA10 | 0.653 | 0.884 | 0.106 | 20 | 10 | 90 | 10 |
| PkHA15 | 1.038 | 1.405 | 0.169 | 25 | 10 | 85 | 15 |
| PkHA20 | 1.470 | 1.991 | 0.239 | 30 | 10 | 80 | 20 |
| PkHA25 | 1.960 | 2.654 | 0.319 | 35 | 10 | 75 | 25 |
| PkHA30 | 2.521 | 3.413 | 0.41 | 40 | 10 | 70 | 30 |
| PkHA35 | 3.167 | 4.288 | 0.515 | 45 | 10 | 65 | 35 |
| PkHA40 | 3.921 | 5.309 | 0.637 | 50 | 10 | 60 | 40 |
| PkHA45 | 4.812 | 6.516 | 0.782 | 60 | 10 | 55 | 45 |
| PkHA50 | 5.882 | 7.964 | 0.956 | 75 | 10 | 50 | 50 |
| PkHA100 | 111.76 | 151.329 | 11.88 | 200 | 0 | 0 | 100 |

*Concentration of $H_3PO_4$
**Additional water is used to control the pH only

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The composite particle samples of Example 1 were ball milled for 2 hrs to form particles. The ball mill was a planetary ball mill at a speed of 350 rpm for 0.5 to 2 hours. The grinding medium was ethanol. The particles were then dried in an oven at 120° C. for 6 hrs. The compositions of the particles were determined by thermal gravimetric analysis, assuming that all of the non-combustible residue was hydroxyapatite, as summarized in FIG. 27A and Table 2.

Figure 2A:
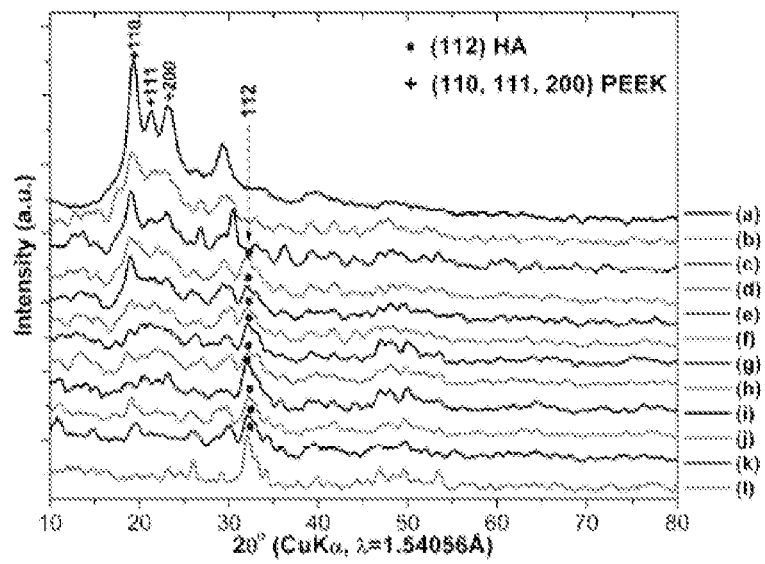
FIG. 2A shows X-ray diffraction intensity as a function of scattering angle for PEEK-hydroxyapatite nanocomposites. Samples IDs are from Table 1: (a) PkHA00, (b) PkHA05, (c) PkHA10, (d) PkHA15, (e) PkHA20, (f) PkHA25, (g) PkHA30, (h) PkHA35, (i) PkHA40, (j) PkHA45, (k) PkHA50, and (l) PkHA100.

The particles were then analyzed by x-ray diffraction (XRD). As shown in FIG. 2A, the intensity of the (112) peak at 2θ≈32.4° increased as the hydroxyapatite content of the pellets increased.

Figure 3A:
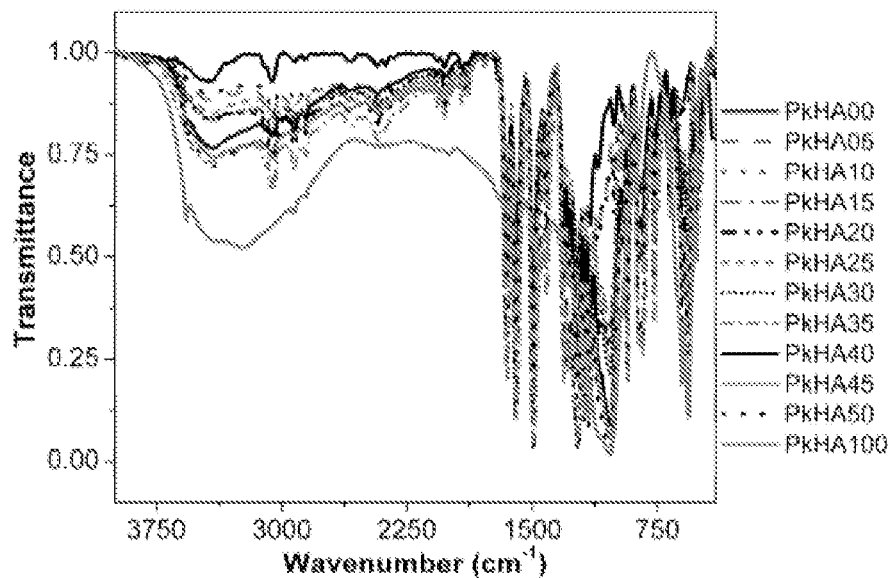
FIG. 3A displays Fourier Transform Infrared (FTIR) spectra for PEEK-hydroxyapatite nanocomposites. Sample IDs are from Table 1.
Figure 3B:
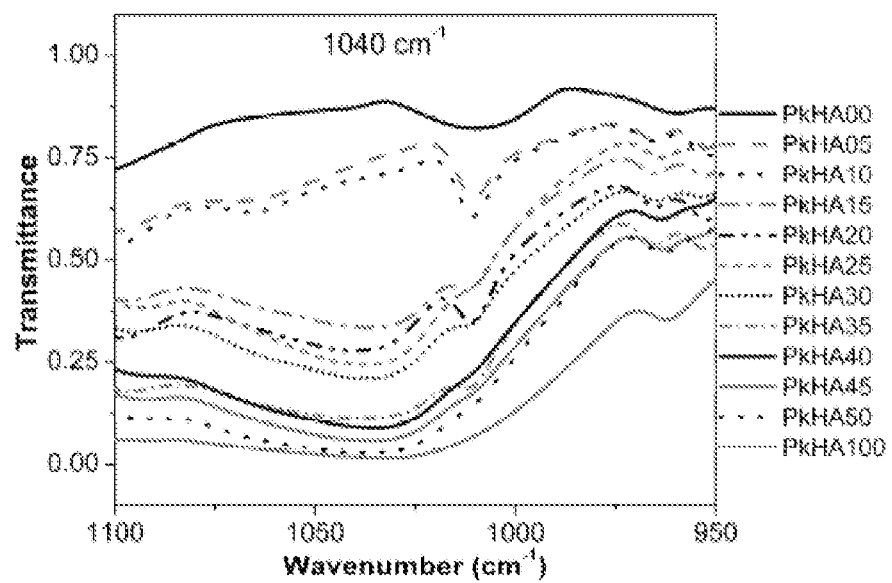
FIGS. 3B and 3C display details of the FTIR spectra of FIG. 3A in the range of 950-1100 $cm^{-1}$ and in the range of 450-650 $cm^{-1}$, respectively.
Figure 3C:
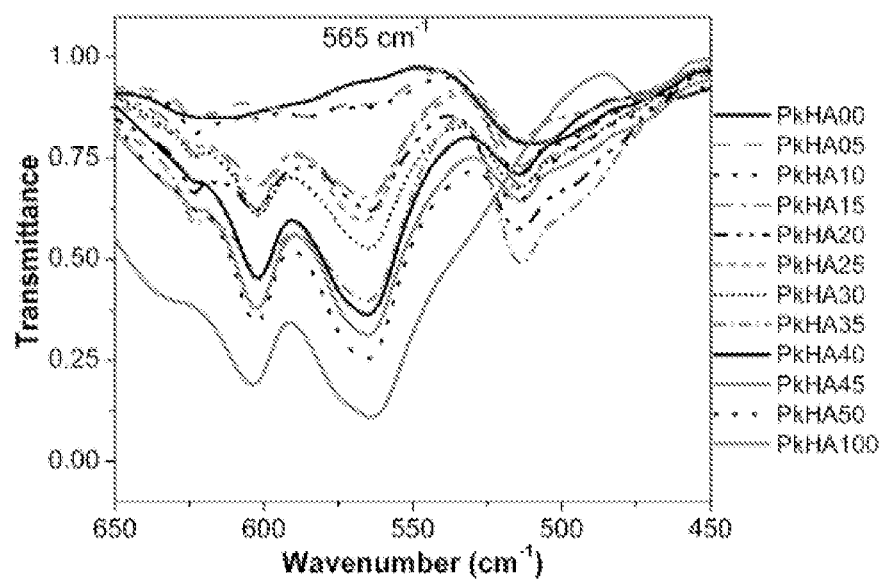

The particles were analyzed by Fourier transform infrared spectroscopy, as shown in FIGS. 3A-3C. All of the infrared peaks of the functional groups in PEEK were present. The peaks at 846 and 1490 cm$^{-1}$ are attributable to the aromatic carbon-carbon double bonds. The peaks at 1226, 1652, and 3062 cm$^{-1}$ are attributable to aromatic ether, carbonyl, and aromatic hydrogen moieties, respectively. The peaks near 565 and 1040 cm$^{-1}$ are attributable to the vibrational mode of the $PO_4^{3-}$ moiety of the hydroxyapatite. The small sharp peak near 3530-3600 cm$^{-1}$ is attributable to the stretching vibration of non-associated, free OH$^-$ from absorbed water, or the hydrated OH$^-$ of the hydroxyapatite. The broad band near 3100-3500 cm$^{-1}$ is attributable to absorbed water for the hydroxyapatite and the molecular OH$^-$ or hydrogen bonding (either inter- or intra-chain) for the PEEK. Note that the size of the 3100-3500 cm$^{-1}$ peak increases as the composite composition becomes richer in hydroxyapatite.

Figure 4A:
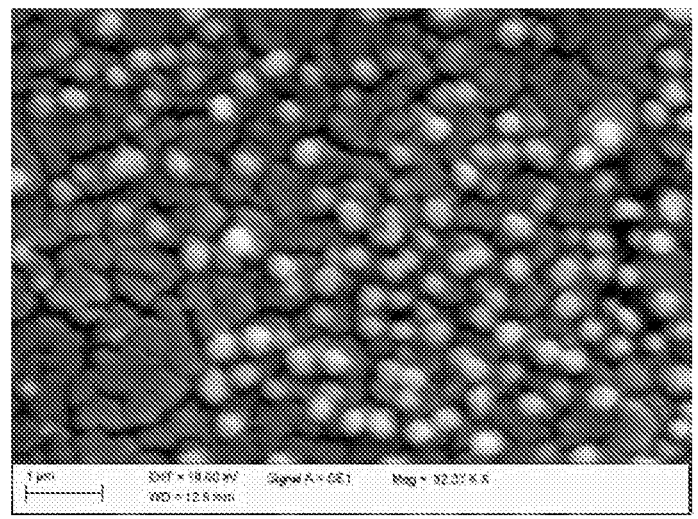
FIG. 4A is a Scanning Electron Microscopy (SEM) image of unsintered PEEK particles.
Figure 4B:
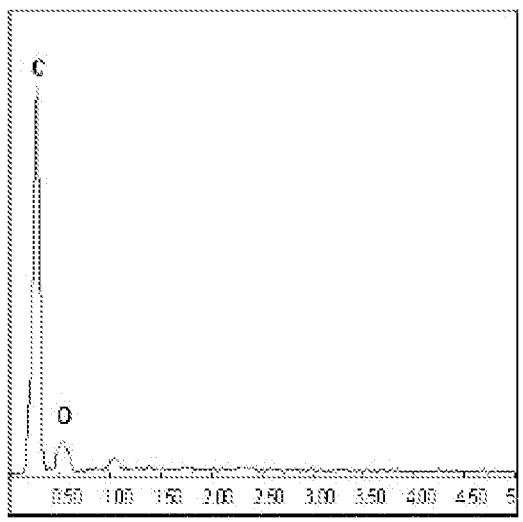
FIG. 4B displays an Electron Dispersive Analysis of X-ray (EDAX) spectrum for unsintered PEEK particles.
Figure 4C:
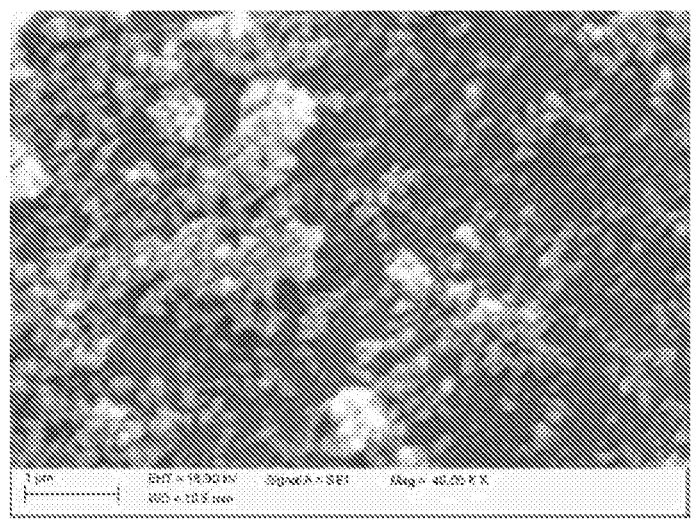
FIG. 4C is a SEM image of unsintered hydroxyapatitite particles.
Figure 4D:
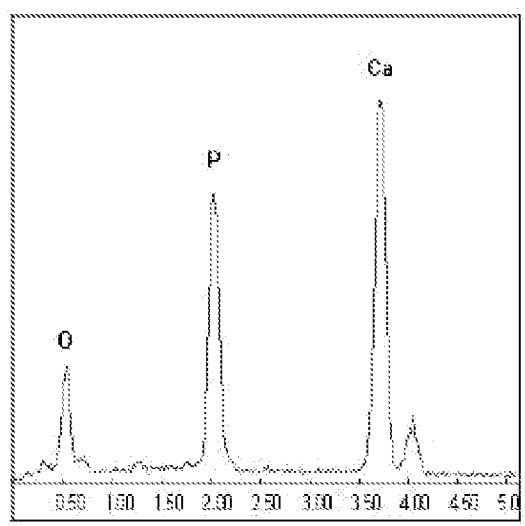
FIG. 4D displays an EDAX spectrum for unsintered hydroxyapatite particles.
Figure 5A:
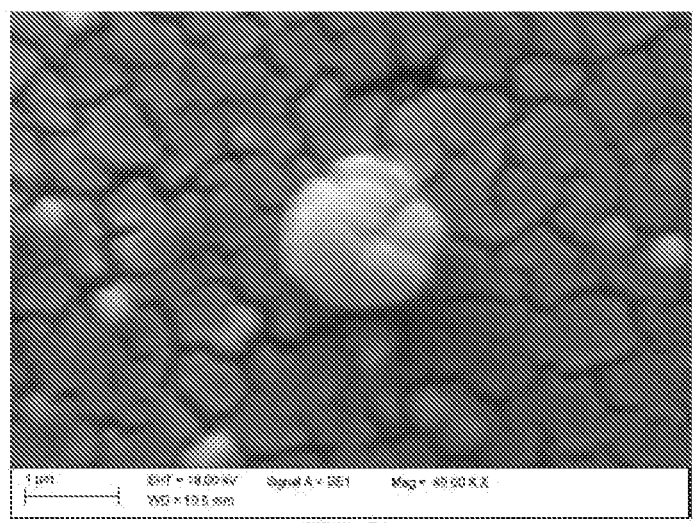
FIG. 5A is a SEM image of unsintered nanocomposite PkHA05 after ball milling 2 hrs.
Figure 5B:
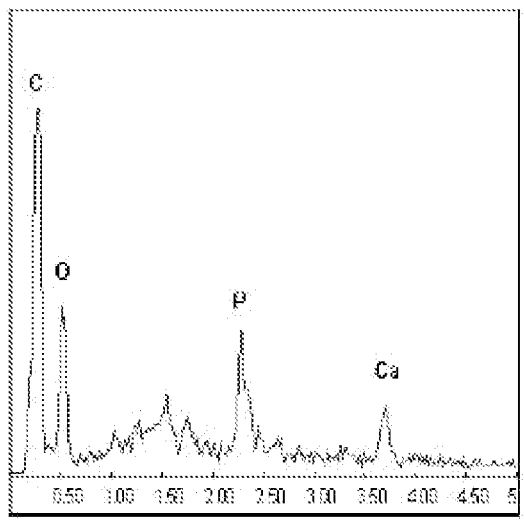
FIG. 5B displays an EDAX spectrum for unsintered nanocomposite PkHA05 after ball milling 2 hrs.
Figure 6A:
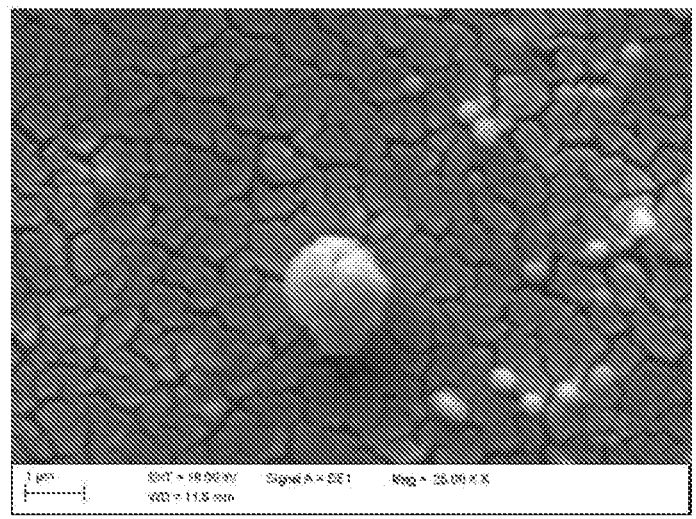
FIG. 6A is a SEM image of unsintered nanocomposite PkHA10 after ball milling 2 hrs.
Figure 6B:
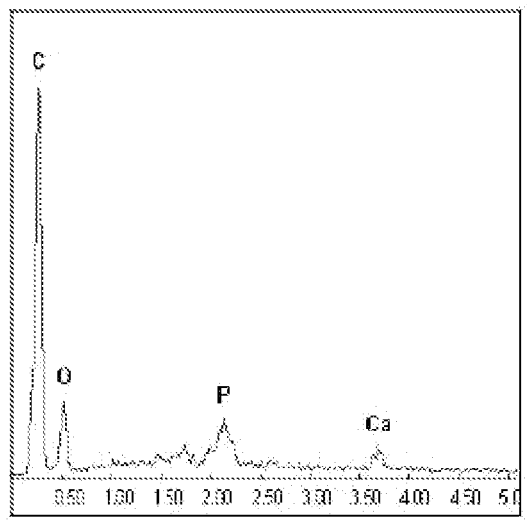
FIG. 6B displays an EDAX spectrum for nanocomposite PkHA10 after ball milling 2 hrs.
Figure 7A:
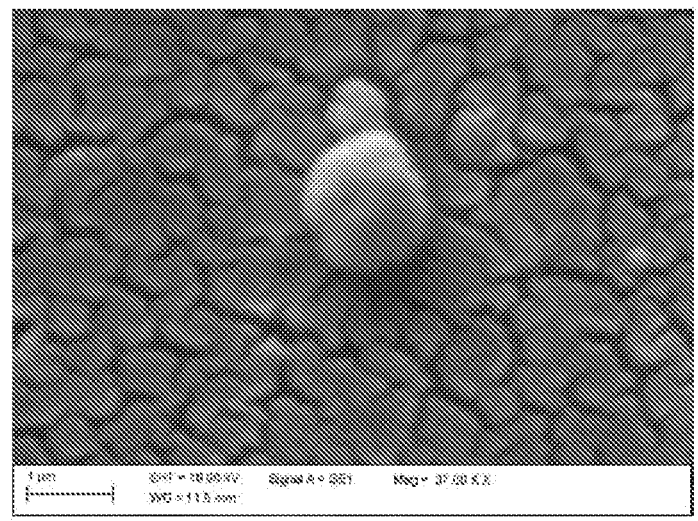
FIG. 7A is a SEM image of unsintered nanocomposite PkHA15 after ball milling 2 hrs.
Figure 7B:
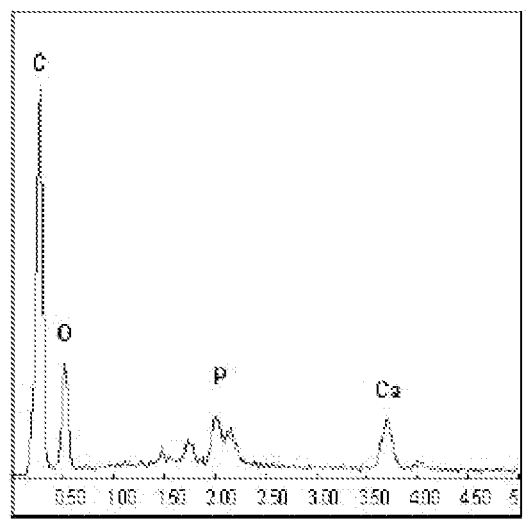
FIG. 7B displays an EDAX spectrum for unsintered nanocomposite PkHA15 after ball milling 2 hrs.
Figure 8A:
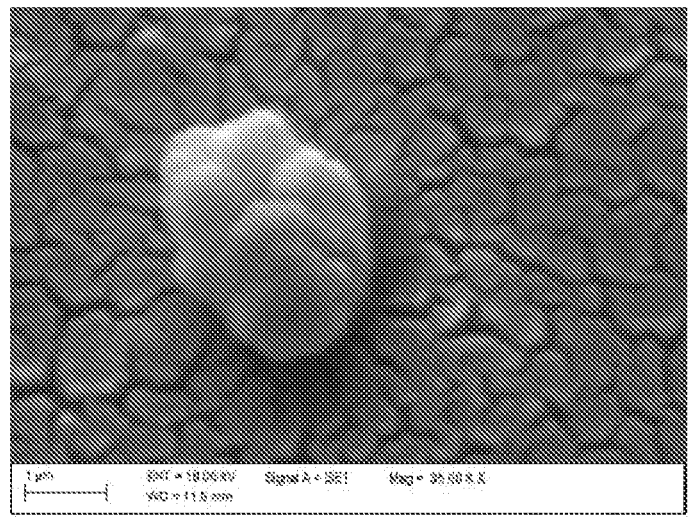
FIG. 8A is a SEM image of nanocomposite PkHA20 after ball milling 2 hrs.
Figure 8B:
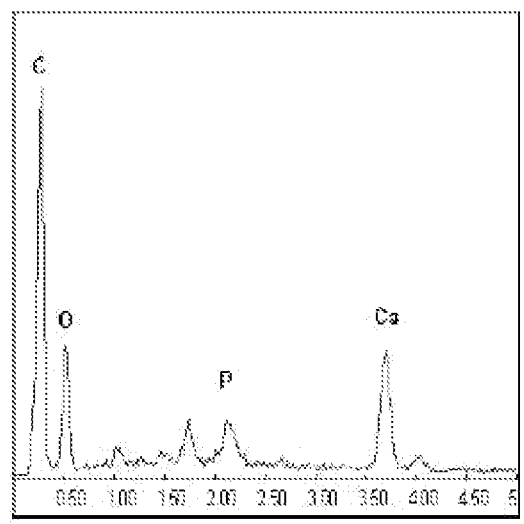
FIG. 8B displays an EDAX spectrum for unsintered nanocomposite PkHA20 after ball milling 2 hrs.
Figure 9A:
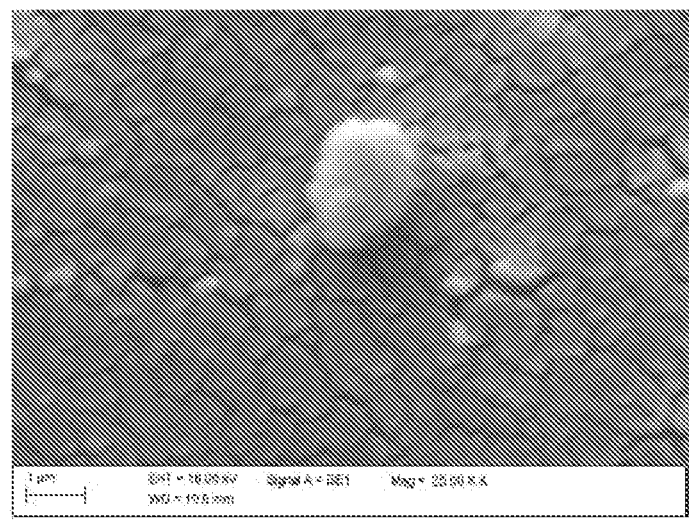
FIG. 9A is a SEM image of unsintered nanocomposite PkHA25 after ball milling 2 hrs.
Figure 9B:
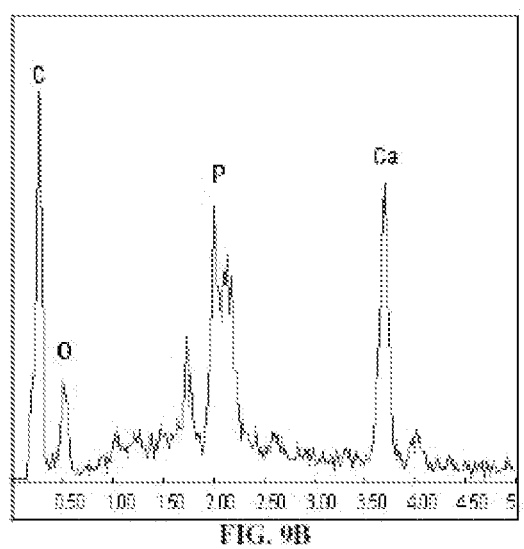
FIG. 9B displays an EDAX spectrum for unsintered nanocomposite PkHA25 after ball milling 2 hrs.
Figure 10A:
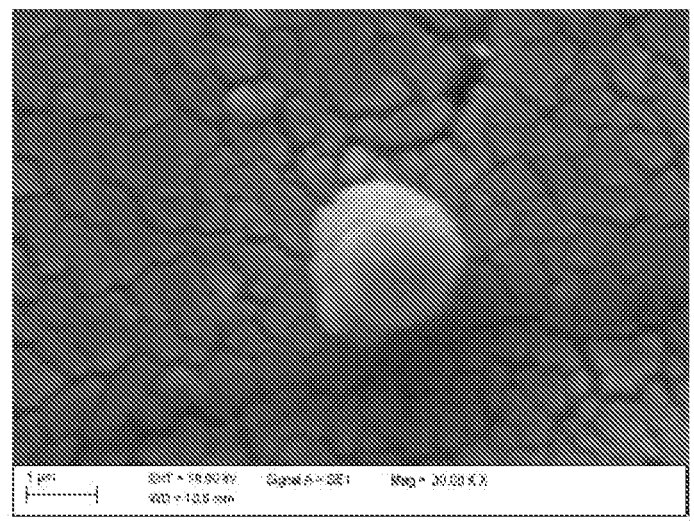
FIG. 10A is a SEM image of unsintered nanocomposite PkHA30 after ball milling 2 hrs.
Figure 10B:
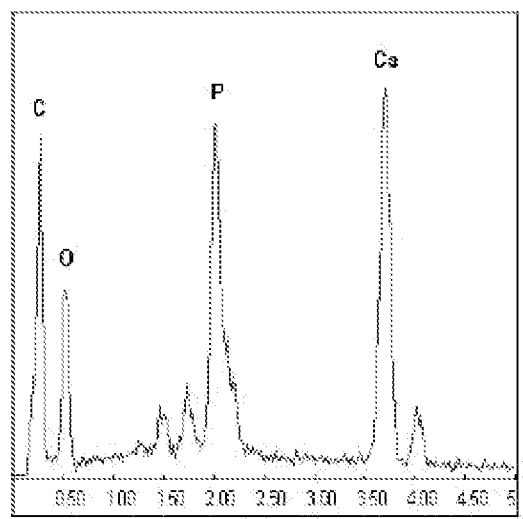
FIG. 10B displays an EDAX spectrum for unsintered nanocomposite PkHA30 after ball milling 2 hrs.
Figure 11A:
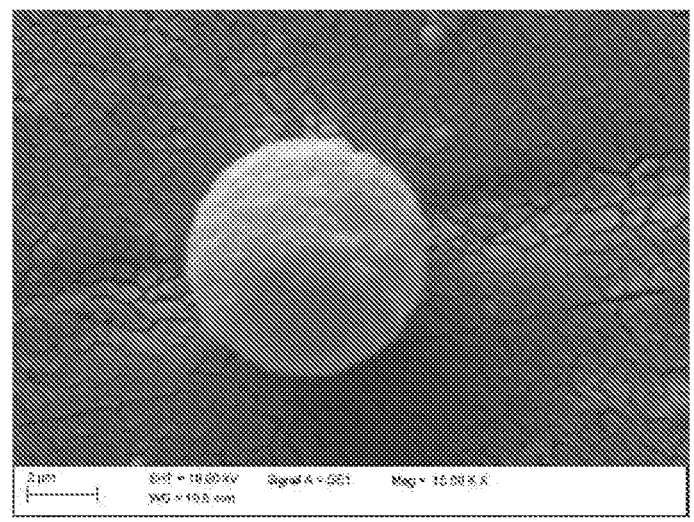
FIG. 11A is a SEM image of unsintered nanocomposite PkHA35 after ball milling 2 hrs.
Figure 11B:
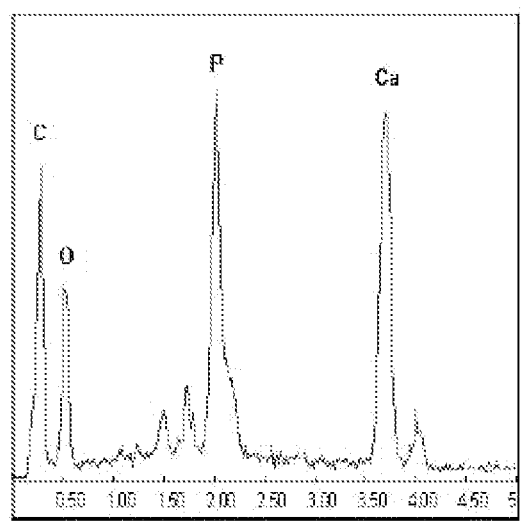
FIG. 11B displays an EDAX spectrum for unsintered nanocomposite PkHA35 after ball milling 2 hrs.
Figure 12A:
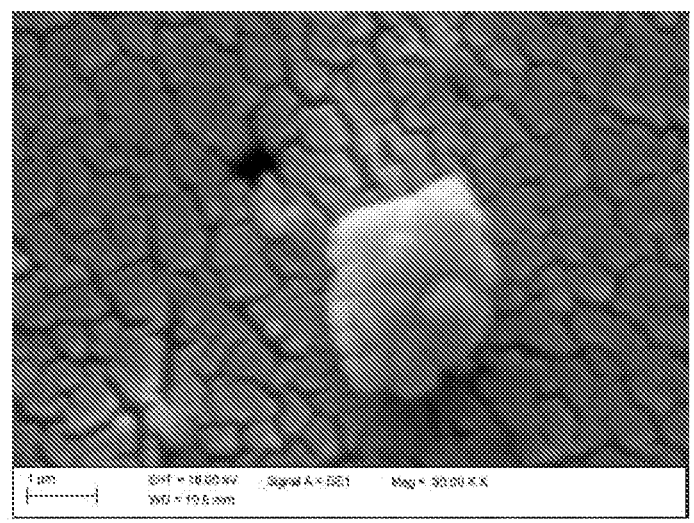
FIG. 12A is a SEM image of unsintered nanocomposite PkHA40 after ball milling 2 hrs.
Figure 12B:
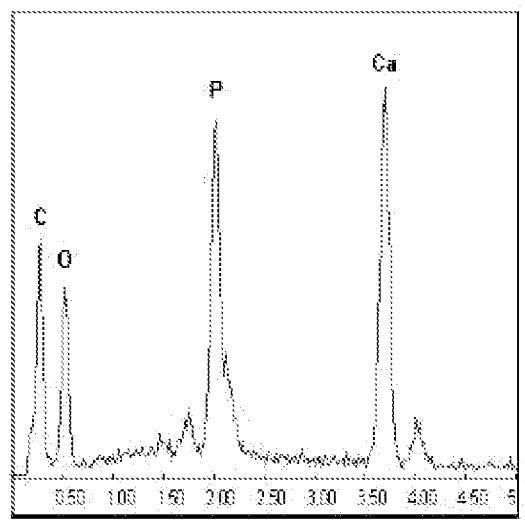
FIG. 12B displays an EDAX spectrum for unsintered nanocomposite PkHA40 after ball milling 2 hrs.
Figure 13A:
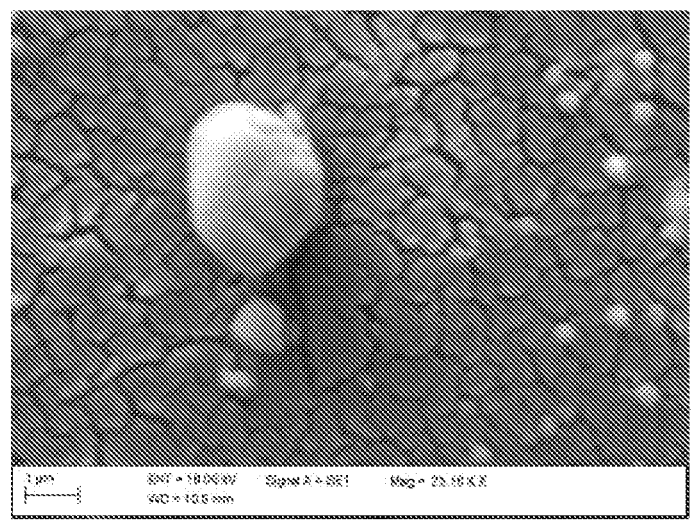
FIG. 13A is a SEM image of unsintered nanocomposite PkHA45 after ball milling 2 hrs.
Figure 13B:
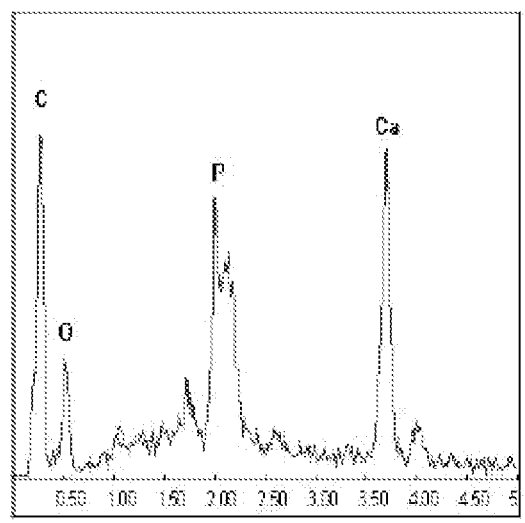
FIG. 13B displays an EDAX spectrum for unsintered nanocomposite PkHA45 after ball milling 2 hrs.
Figure 14A:
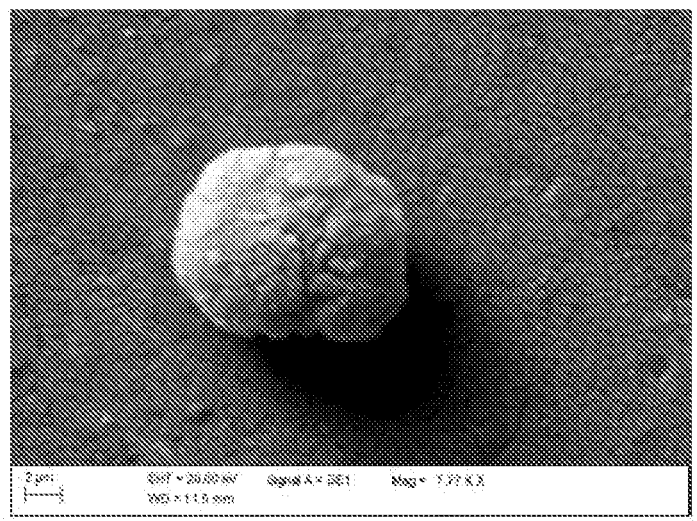
FIG. 14A is a SEM image of unsintered nanocomposite PkHA50 after ball milling 2 hrs.
Figure 14B:
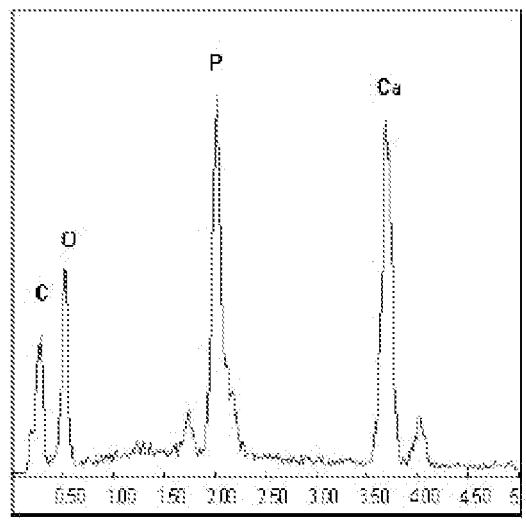
FIG. 14B displays an EDAX spectrum for unsintered nanocomposite PkHA50 after ball milling 2 hrs.

Nucleation and growth of the unsintered nanocomposites were studied by scanning electron microscopy. FIGS. 4A and 4B show pure PEEK and hydroxyapatite particles, respectively. The PEEK particles were approximately spherical in shape, with approximate diameter from 400 nm to 2 micrometers. The hydroxyapatite particles were also approximately spherical in shape, with approximate diameter less than 100 nm. FIGS. 5A, 6A, 7A, 8A, 9A, 10A, 11A, 12A, 13A, and 14A show the unsintered nanocomposites after ball milling for 2 hrs. These were generally larger than either the pure PEEK or hydroxyapatite particles.

Figure 15A:
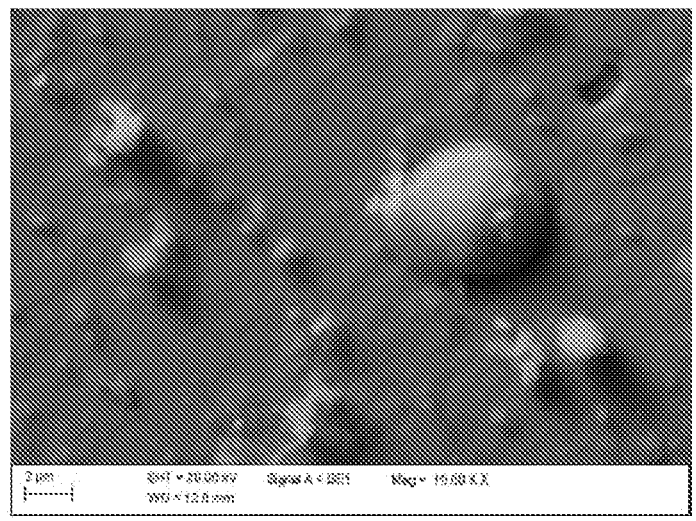
FIGS. 15A and 15B are SEM images of unsintered nanocomposite PkHA30 after 1 hr of precipitation and after 2 hrs of precipitation, respectively.
Figure 15B:
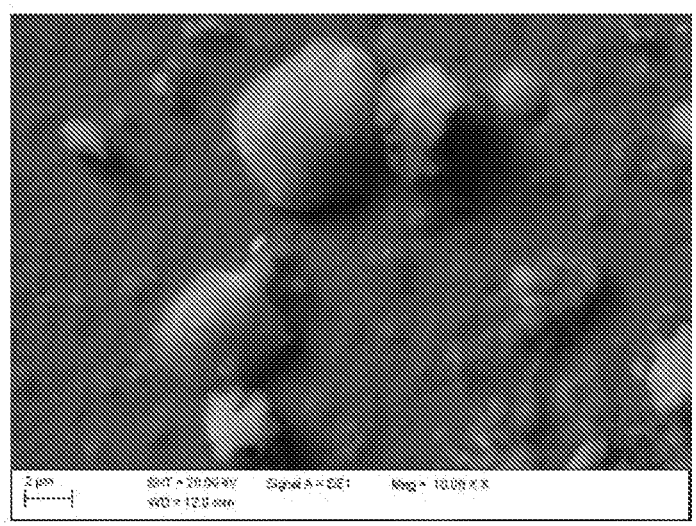
Figure 16A:
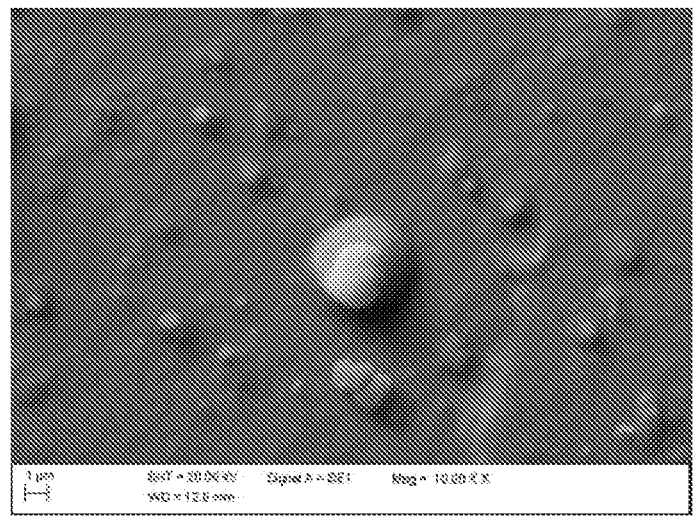
FIGS. 16A, 16B, 16C, and 16D are SEM images of unsintered nanocomposite PkHA30 after ball milling 30 min, 1 hr, 90 minutes, and 2 hr, respectively.
Figure 16B:
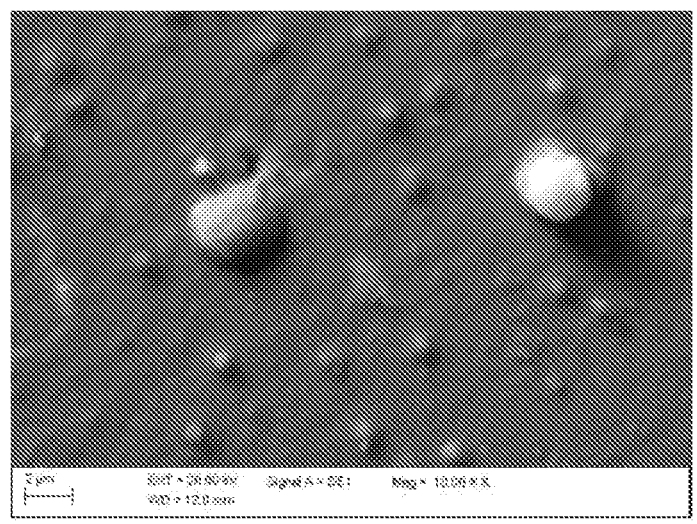
Figure 16C:
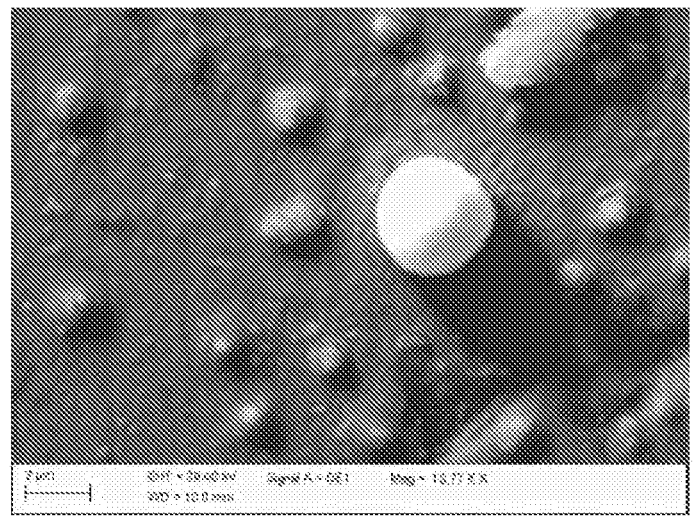
Figure 16D:
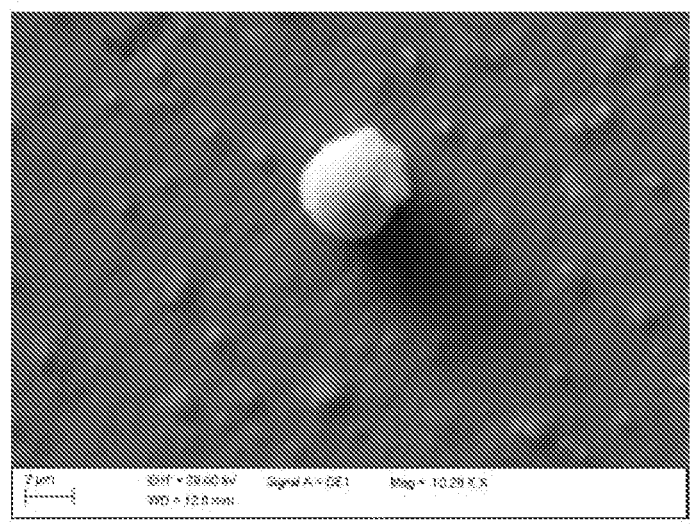

FIGS. 15A-15B are scanning electron micrographs of the unsintered PkHA30 nanocomposite during precipitation, prior to ball milling. Some hydroxyapatite particles agglomerated during precipitation. At least some hydroxyapatite nucleation appears to have occurred separately from the PEEK particle surface. FIGS. 16A-16D are scanning electron micrographs of hydroxyapatite nanocrystal nucleation and growth on the PEEK particle surface. The growth mechanism appears to have been similar to that of biomimitic growth of host tissues on biomaterials. As milling time increased, more of the PEEK particle surface was covered with hydroxyapatite nanocystals, until substantially all of the PEEK particle surface core was surrounded by hydroxyapatite nanocrystals as a shell. FIG. 16D shows a PEEK particle that appears to have been completely surrounded by hydroxyapatite nanocrystals after 2 hrs of milling time.

Figure 17A:
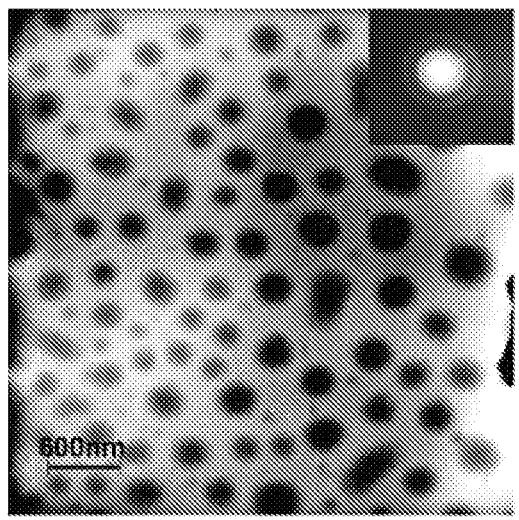
FIGS. 17A and 17B are Transmission Electron Microscopy (TEM) images and diffraction patterns (inset) of unsintered PEEK particles and unsintered hydroxyapatite particles, respectively.
Figure 17B:
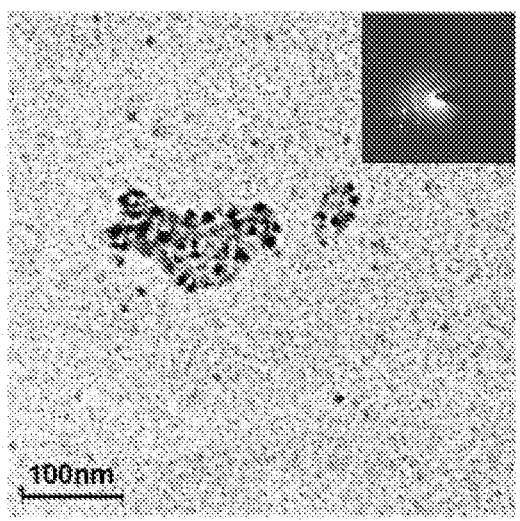
Figure 18A:
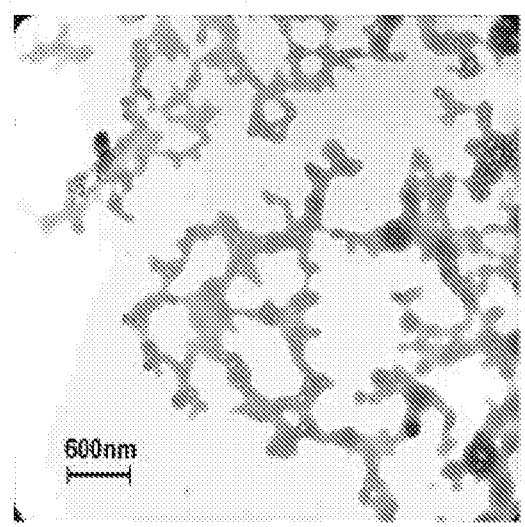
FIGS. 18A and 18B are TEM images of unsintered nanocomposites PkHA05 PkHA10, respectively.
Figure 18B:
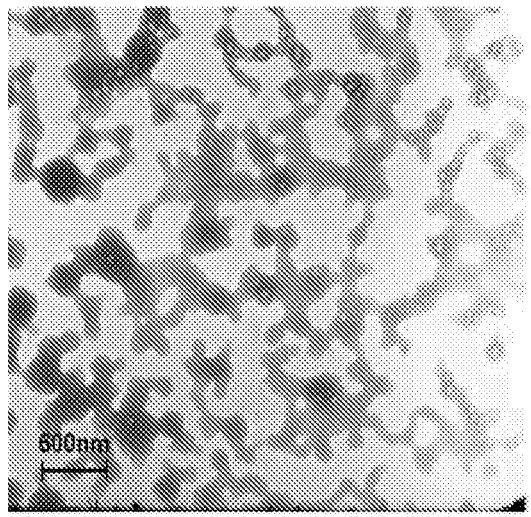
Figure 19A:
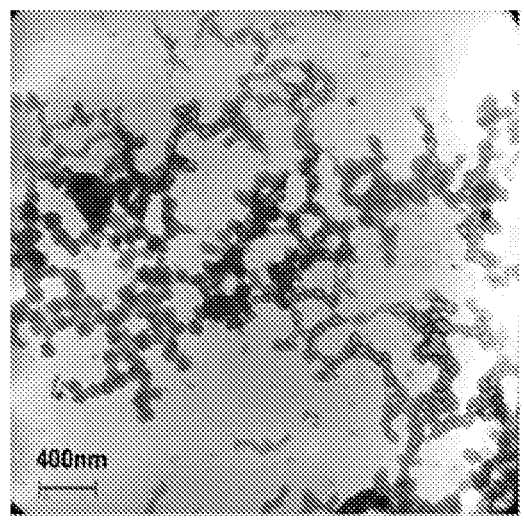
FIGS. 19A and 19B are TEM images of unsintered nanocomposites PkHA15 and PkHA20, respectively.
Figure 19B:
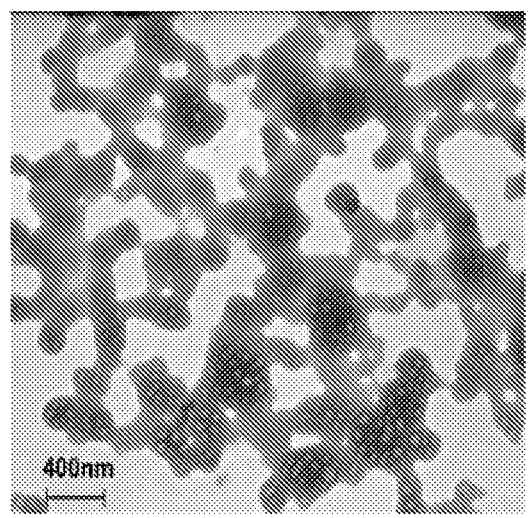
Figure 20A:
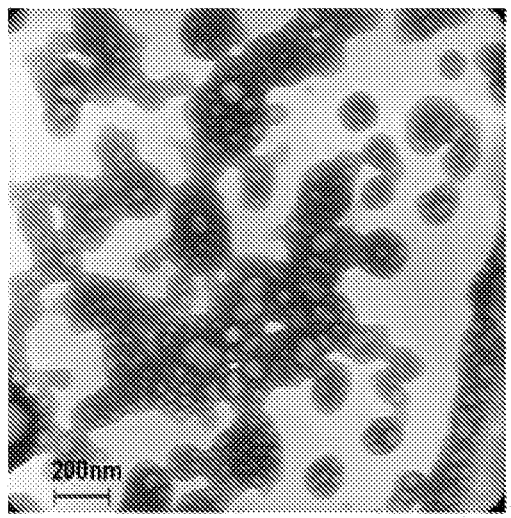
FIGS. 20A and 20B are TEM images of unsintered nanocomposites PkHA25 and PkHA30, respectively.
Figure 20B:
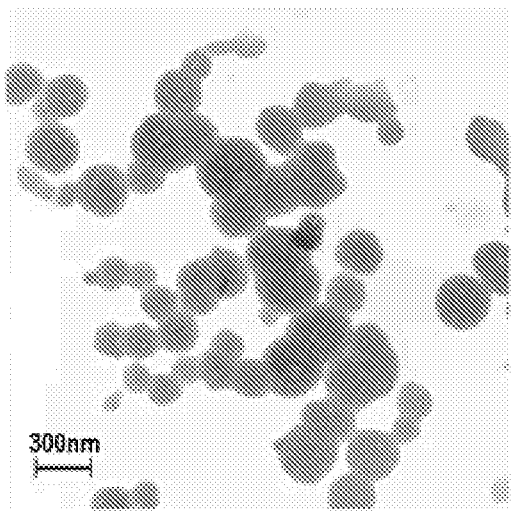
Figure 21A:
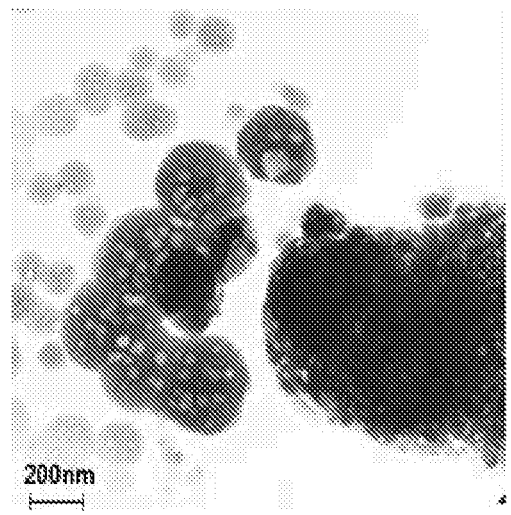
FIGS. 21A and 21B are TEM images of unsintered nanocomposites PkHA35 and PkHA40, respectively.
Figure 21B:
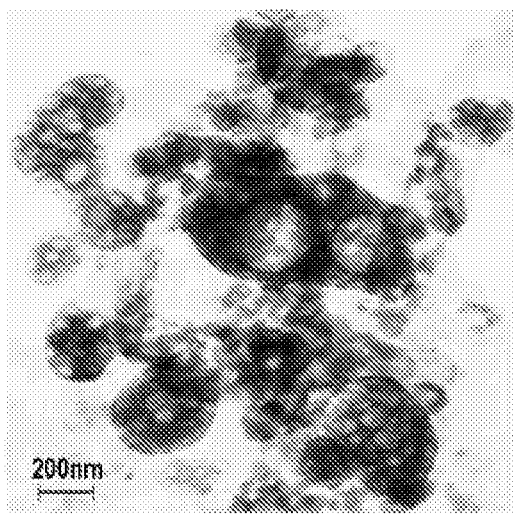
Figure 22A:
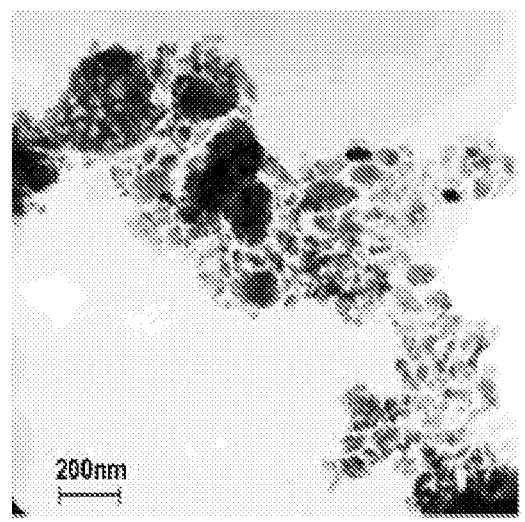
FIGS. 22A and 22B are TEM images of unsintered nanocomposites PkHA45 and PkHA50, respectively.
Figure 22B:
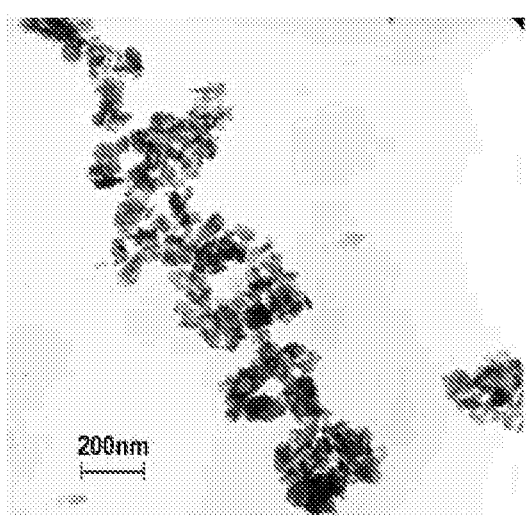

Nucleation and growth of the unsintered nanocomposites were also studied by transmission electron microscopy. FIGS. 17A and 17B show unsintered PEEK and hydroxyapatite particles, respectively. The PEEK particles were approximately spherical in shape, with approximate diameter from 200 nm to 500 nm. The hydroxyapatite particles were also approximately spherical in shape, with approximate diameter less than 50 nm. FIGS. 18A-22B show the unsintered nanocomposites after ball milling for 2 hrs. These were generally larger than either the unsintered PEEK or hydroxyapatite particles.

Figure 23A:
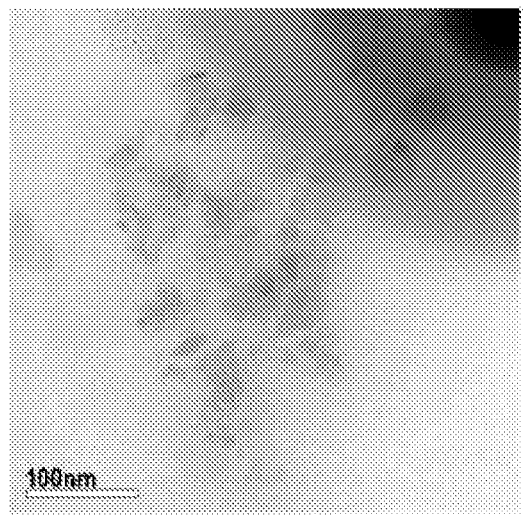
FIGS. 23A and 23B are TEM images of unsintered nanocomposite PkHA30 after 1 hr of precipitation and after 2 hrs of precipitation, respectively.
Figure 23B:
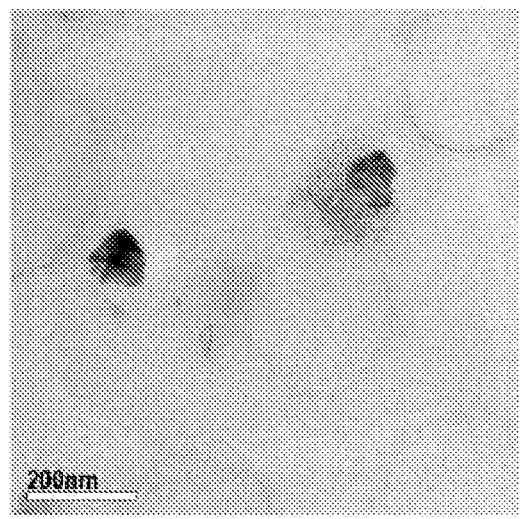
Figure 24A:
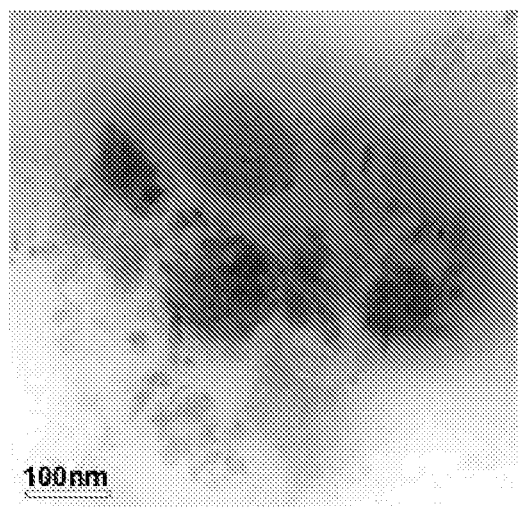
FIGS. 24A, 24B, 24C, and 24D are TEM images of unsintered nanocomposite PkHA30 after ball milling 30 min, 1 hr, 90 min, and 2 hrs, respectively.
Figure 24B:
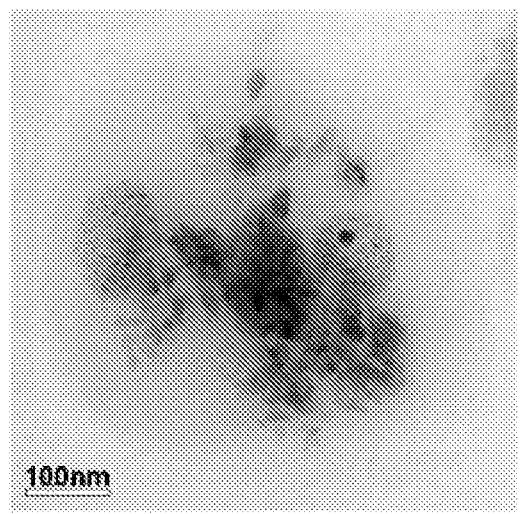
Figure 24C:
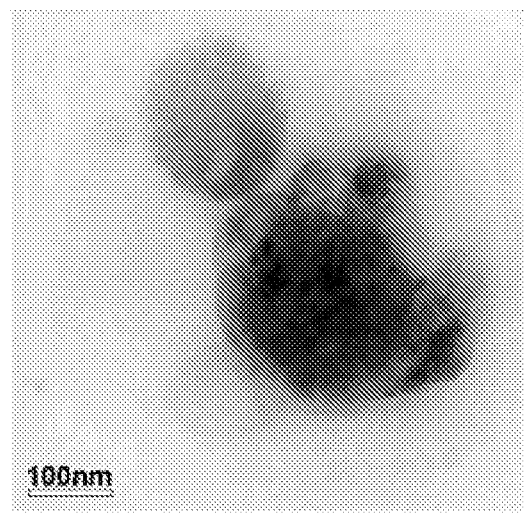
Figure 24D:
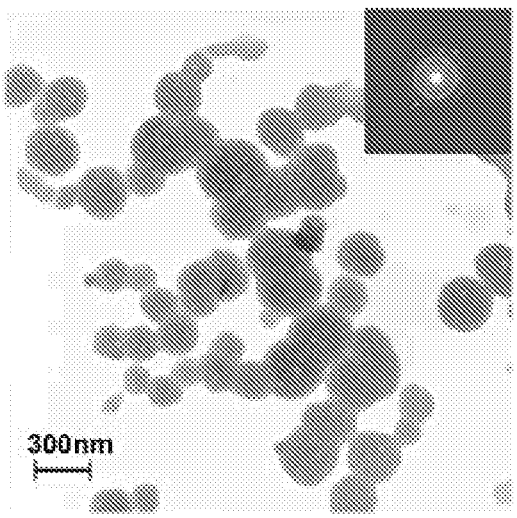

FIGS. 23A-23B are transmission electron micrographs of the unsintered PkHA30 nanocomposite during precipitation, prior to ball milling. Some hydroxyapatite particles agglomerated during precipitation. At least some hydroxyapatite nucleation appears to have occurred separately from the PEEK particle surface. FIGS. 24A-24D are transmission electron micrographs of hydroxyapatite nanocrystal nucleation and growth on the PEEK particle surface. The growth mechanism appears to have been similar to that of biomimitic growth of host tissues on biomaterials. As milling time increased, more of the PEEK particle surface was covered with hydroxyapatite nanocrystals, until substantially all of the PEEK particle surface core was surrounded by hydroxyapatite nanocrystals as a shell. FIG. 24D shows a PEEK particle that appears to have been completely surrounded by hydroxyapatite nanocrystals after 2 hrs of milling time.

Coincident with scanning electron microscopy, the elemental compositions of the unsintered nanocomposites were determined using Electron Dispersive Analysis of X-ray (EDAX). The EDAX spectra show the relative intensities vs. energy (keV) for each element present in the unsintered nanocomposites. The spectra are shown in FIGS. 5B, 6B, 7B, 8B, 9B, 10B, 11B, 12B, 13B, and 14B, and the results are summarized in Table 3. The major peaks in the spectra were attributable to atoms of carbon, oxygen, phosphorous, and calcium. A very weak peak near 1.6 keV is thought to be due to the aluminum substrate on which the particles were disposed. These spectra show that the atomic ratio of Ca to P increased with increasing hydroxyapatite concentration in the nanocomposites, over a range of 1.5 to 1.8, with the value of 1.663 for the PkHA30 sample being closest to the theoretical ratio of 5/3 based on the chemical formula for the hydroxyapatite. The EDAX spectrum for the PkHA30 sample was also very close to the theoretical spectrum for a 30 wt % hydroxyapatite nanocomposite particle, based on the theoretical atomic percentages for PEEK and hydroxyapatite: 25.56% observed vs. 27.65% theoretical for O, 64.08% observed vs. 61.29% theoretical for C, 6.47% observed vs. 6.91% theoretical for Ca, and 3.89% observed vs. 4.15% theoretical for P.

TABLE 2

Compositions of Unsintered Pellets by TGA

| Sample ID | PEEK (wt %) | Hydroxyapatite (wt %) |
|---|---|---|
| PkHA00 | 100 | 0 |
| PkHA05 | 92.3 | 7.7 |
| PkHA10 | 89.4 | 10.6 |
| PkHA15 | 85.1 | 14.9 |
| PkHA20 | 80.1 | 19.9 |
| PkHA25 | 71.9 | 28.1 |
| PkHA30 | 69.9 | 30.1 |
| PkHA35 | 67.9 | 32.1 |
| PkHA40 | 63.0 | 37.0 |
| PkHA45 | 51.8 | 48.2 |
| PkHA50 | 40.6 | 59.4 |
| PkHA100 | 0 | 100 |

TABLE 3

Elemental Analysis of Unsintered Pellets by EDAX

| Sample | Unit | O | C | Ca | P | Ca/P |
|---|---|---|---|---|---|---|
| PkHA00 | (wt %) | 15.03 | 84.97 | 0 | 0 | |
| | (At %) | 11.71 | 88.29 | 0 | 0 | — |
| PkHA05 | (wt %) | 20.05 | 73.65 | 4.16 | 2.14 | |
| | (At %) | 16.57 | 81.15 | 1.37 | 0.91 | 1.505 |
| PkHA10 | (wt %) | 19.37 | 67.16 | 8.97 | 4.50 | |
| | (At %) | 16.87 | 77.98 | 3.12 | 2.03 | 1.544 |
| PkHA15 | (wt %) | 21.57 | 62.03 | 11.08 | 5.32 | |
| | (At %) | 19.35 | 74.21 | 3.98 | 2.46 | 1.618 |
| PkHA20 | (wt %) | 23.32 | 54.70 | 14.86 | 7.12 | |
| | (At %) | 22.03 | 68.89 | 5.61 | 3.47 | 1.617 |
| PkHA25 | (wt %) | 25.72 | 50.78 | 15.96 | 7.54 | |
| | (At %) | 24.80 | 65.29 | 6.16 | 3.75 | 1.642 |

TABLE 3-continued

Elemental Analysis of Unsintered Pellets by EDAX

| Sample | Unit | O | C | Ca | P | Ca/P |
|---|---|---|---|---|---|---|
| PkHA30 | (wt %) | 26.26 | 49.38 | 16.62 | 7.74 | |
| | (At %) | 25.56 | 64.08 | 6.47 | 3.89 | 1.663 |
| PkHA35 | (wt %) | 29.96 | 40.38 | 20.32 | 9.34 | |
| | (At %) | 30.97 | 55.65 | 8.40 | 4.98 | 1.687 |
| PkHA40 | (wt %) | 29.84 | 39.94 | 20.72 | 9.50 | |
| | (At %) | 30.99 | 55.31 | 8.61 | 5.09 | 1.690 |
| PkHA45 | (wt %) | 28.93 | 40.10 | 21.32 | 9.65 | |
| | (At %) | 30.16 | 55.74 | 8.91 | 5.19 | 1.717 |
| PkHA50 | (wt %) | 36.11 | 19.78 | 30.69 | 13.42 | |
| | (At %) | 44.20 | 32.29 | 15.03 | 8.48 | 1.772 |
| PkHA100 | (wt %) | 40.44 | 0 | 40.58 | 18.98 | |
| | (At %) | 60.84 | 0 | 24.42 | 14.74 | 1.657 |

Example 2

Preparation of Un-Sintered Pellets

The particles of Example 1 were poured into the steel moulds to make pellets using 300 MPa by uniaxial hot press at 150° C.

Example 3

Preparation of Sintered Pellets

The pellets of Example 2 were sintered by successive heating for 3 hours at 320° C., for 2 hours at 345° C., and for 90 μm at 370° C. The composite pellets were deposited in an alumina crucible covered with alumina lid and this was then successively heated at 320° C. for 3 hrs, 345° C. for 2 hrs, and 370° C. for 90 mins. The sintering was carried out at atmospheric pressure with slow heating rate or ramp rate of 2 to 3° C./min.

Figure 2B:
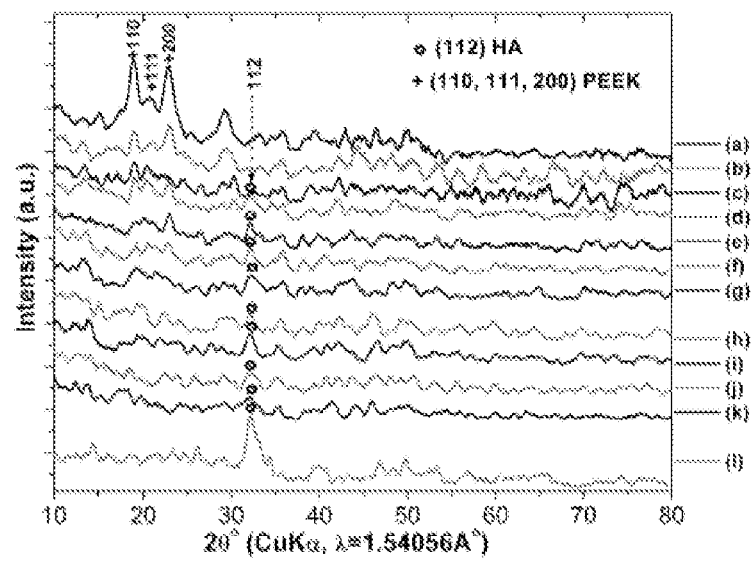
FIG. 2B shows X-ray diffraction intensity as a function of scattering angle for PEEK-hydroxyapatite nanocomposites. Samples IDs are from Table 4: (a) SPkHA00, (b) SPkHA05, (c) SPkHA10, (d) SPkHA15, (e) SPkHA20, (f) SPkHA25, (g) SPkHA30, (h) SPkHA35, (i) SPkHA40, (j) SPkHA45, (k) SPkHA50, and (l) SPkHA100.

The compositions of the sintered pellets were determined by thermal gravimetric analysis, assuming that all of the non-combustible residue was hydroxyapatite, as summarized in FIG. 27B and Table 4. (The Sample IDs in Table 4 correspond to those in Table 1, but have had an "S" appended to them.) The sintered pellets were also analyzed by X-ray diffraction. As shown in FIG. 2B, the intensity of the (112) peak at 2θ≈32.4° increases as hydroxyapatite content of the pellets increases.

Figure 25A:
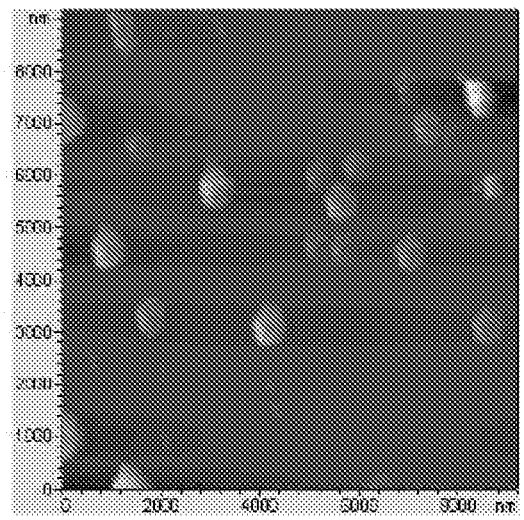
FIGS. 25A, 25B, and 25C are Atomic Force Microscopy (AFM) images of unsintered spherical PEEK particles, unsintered branch-shaped cluster of PEEK particles, and unsintered hydroxyapatite particles, respectively.
Figure 25B:
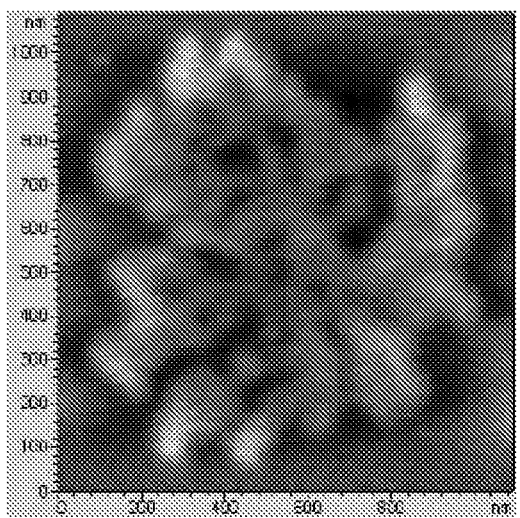
Figure 25B:
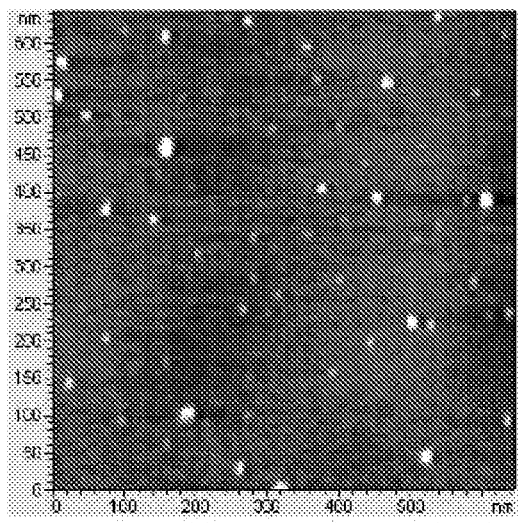
Figure 26A:
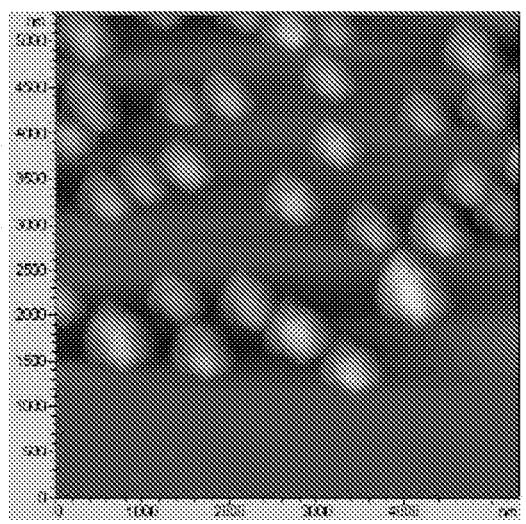
FIGS. 26A, 26B, and 26C are AFM images of sintered PEEK, hydroxyapatite, and nanocomposite SPkHA30 particles, respectively.
Figure 26B:
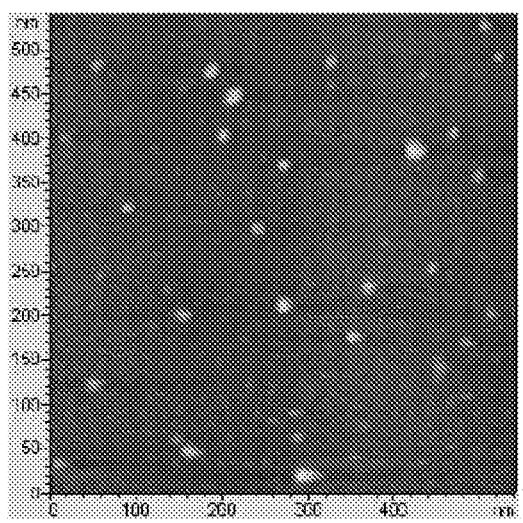
Figure 26C:
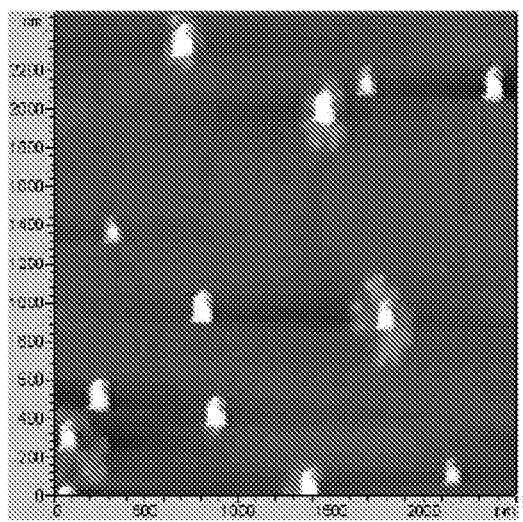
Figure 25C:
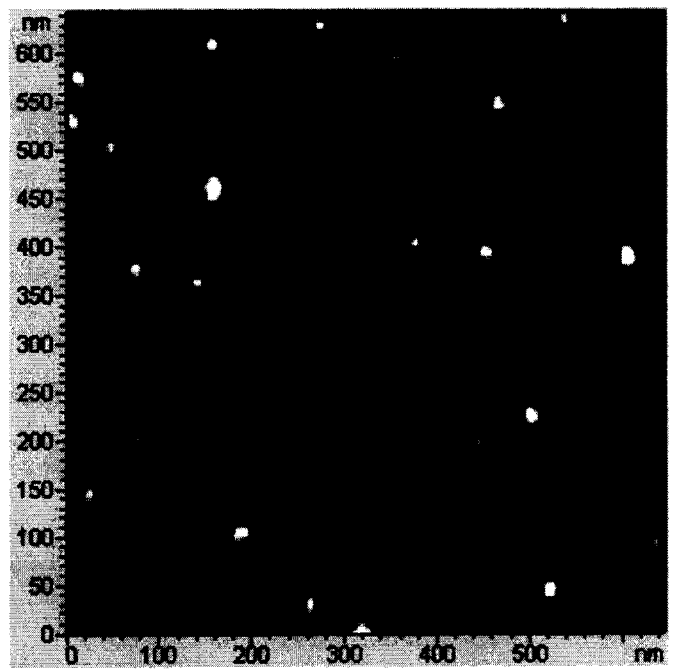
Figure 26A:
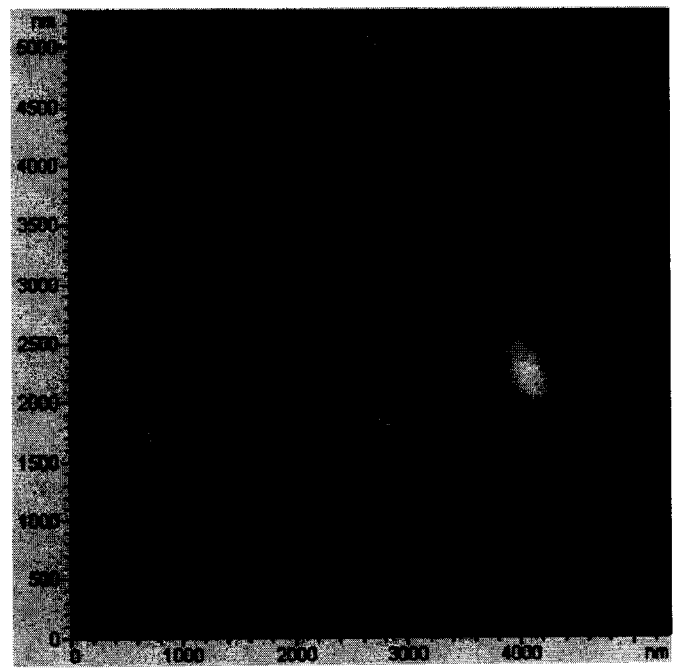
Figure 27A:
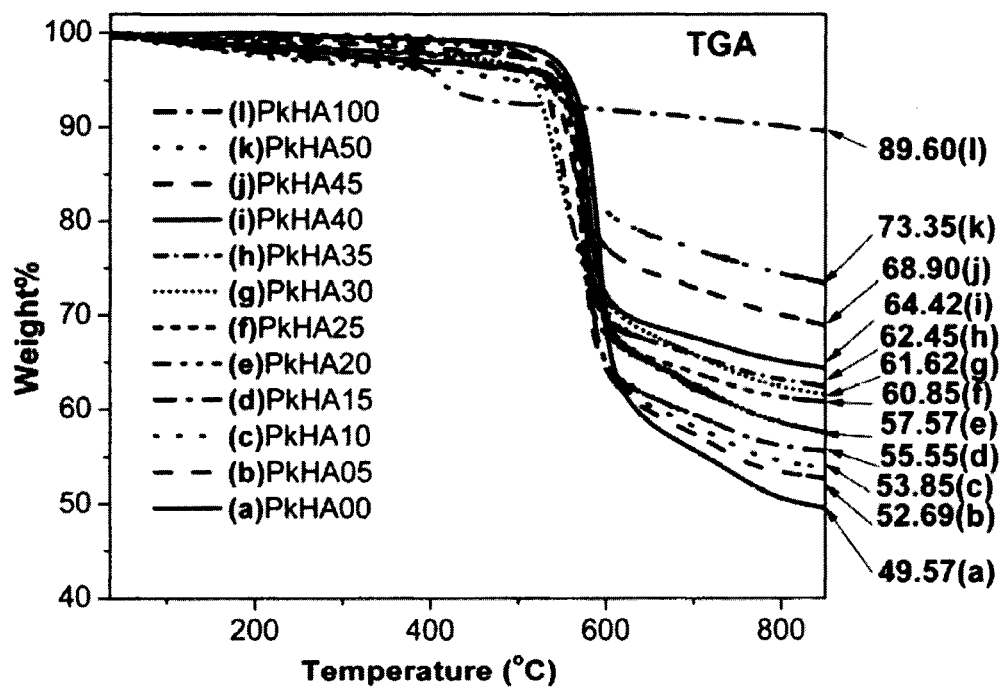
Figure 27B:
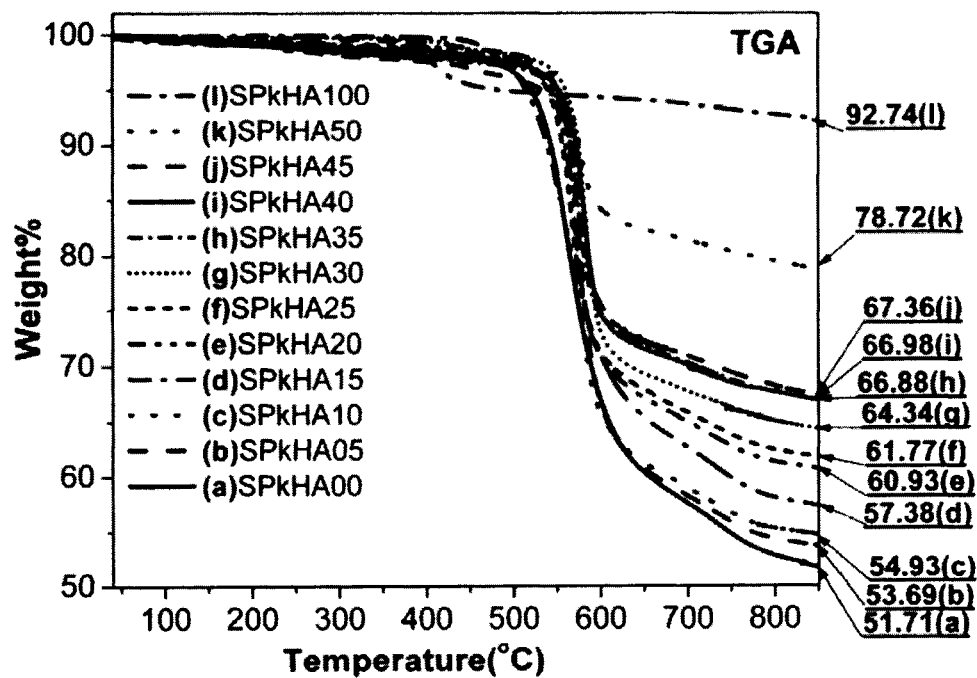

Atomic force microscopy (AFM) was used to further characterize the sintered pellets. FIGS. 25A-25C depict AFM images of unsintered PEEK particles, branch-shaped clusters of unsintered PEEK particles, and unsintered hydroxyapatite particles, respectively. FIGS. 26A-26C depict AFM images of sintered PEEK particles, sintered hydroxyapatite particles, and sintered SPkHA30 nanocomposite powders, respectively. The AFM image for the nanocomposite does not show any loosely bonded hydroxyapatite, but instead suggests a strong bond between the PEEK and hydroxyapatite particles after sintering.

TABLE 4

Compositions of Sintered Pellets as Measured by TGA

| Sample ID | PEEK (wt %) | Hydroxyapatite (wt %) |
|---|---|---|
| SPkHA00 | 100 | 0 |
| SPkHA05 | 94.8 | 5.2 |
| SPkHA10 | 92.1 | 7.9 |
| SPkHA15 | 85.8 | 14.2 |
| SPkHA20 | 77.6 | 22.4 |
| SPkHA25 | 75.5 | 24.5 |
| SPkHA30 | 69.2 | 30.8 |
| SPkHA35 | 63.1 | 36.9 |
| SPkHA40 | 62.8 | 37.2 |
| SPkHA45 | 61.9 | 38.1 |
| SPkHA50 | 34.2 | 65.8 |
| SPkHA100 | 0 | 100 |

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

What is claimed is:
1. A method comprising:
   precipitating a calcium apatite particle from a solution onto a surface of a polymer particle to form a composite particle, forming a pellet comprising at least two of the composite particles; and sintering the pellet in at least a first and a second stage to form a sintered pellet; wherein:

the solution comprises water, calcium oxide, and phosphoric acid;

the first stage is performed at a temperature below a melting temperature of the polymer particle; and the second stage is performed at a temperature above the melting temperature of the polymer particle.

2. The method of claim 1, wherein the polymer particle is between 200 nm and 2 microns in diameter.

3. The method of claim 1, wherein the polymer particle comprises polyetheretherketone and the calcium apatite particle comprises hydroxyapatite, which is nanocrystalline and size of 5 nm to 100 nm.

4. The method of claim 1, wherein the forming comprises milling the composite particle.

5. The method of claim 1, wherein the composite particle is a nanocomposite particle.

6. The method of claim 1, wherein the composite particle comprises a ratio of calcium to phosphorous atoms between 1.5 and 1.8.

7. The method of claim 1, wherein the composite particle comprises at least 40 wt % of the polymer and less than 60 wt % of the calcium apatite.

8. The method of claim 1, wherein the pellet includes a shell surrounding a core, wherein the shell includes the calcium apatite and the core comprises the polymer.

9. The method of claim 1, wherein the sintering comprises liquid sintering.

10. The method of claim 1, wherein the sintered pellet comprises at least 50 wt % of the polymer and less than 50 wt % of the calcium apatite.

11. The method of claim 1, wherein the polymer particle comprises polyetheretherketone.

12. The method of claim 1, wherein the polymer comprises polyetheretherketone, the first stage is performed at about 320° C. and the second stage is performed at a temperature of about 345° C.

13. The method of claim 1 further comprising sintering in a third stage at a temperature of about 370° C.

\* \* \* \* \*

UNITED STATES PATENT AND TRADEMARK OFFICE
CERTIFICATE OF CORRECTION

PATENT NO. : 8,652,373 B2
APPLICATION NO. : 13/147502
DATED : February 18, 2014
INVENTOR(S) : Kar et al.

It is certified that error appears in the above-identified patent and that said Letters Patent is hereby corrected as shown below:

Title Page, Item (56), under "OTHER PUBLICATIONS", in Column 2, Line 2, delete "Hydroxyapaite"" and insert -- Hydroxyapatite" --, therefor.

Title Page, Item (56), under "OTHER PUBLICATIONS", in Column 2, Line 7, delete "Hydroxyapatite-Poly(ether ether ketone) Nanocomposite: Acellular" and insert -- Hydroxyapatite-Poly(etheretherketone) Nanocomposite: A cellular --, therefor.

In the Drawings

Delete Drawing Sheet 30 of 32 and Drawing Sheet 32 of 32 and substitute therefor with the attached Drawing Sheet 30 of 32 and Drawing Sheet 32 of 32.

In the Specification

In Column 3, Line 54, delete "hydroxyapatitite" and insert -- hydroxyapatite --, therefor.

In Column 4, Line 42, delete "PkHA05 PkHA10," and insert -- PkHA05 and PkHA10, --, therefor.

In Column 16, Line 62, insert -- Other embodiments are set forth in the following claims. --.

Signed and Sealed this
Third Day of March, 2015

Michelle K. Lee
*Deputy Director of the United States Patent and Trademark Office*